United States Patent [19]

Frelinger, III et al.

[11] Patent Number: 5,284,751
[45] Date of Patent: Feb. 8, 1994

[54] ANTIBODIES THAT BIND TO A LIGAND-INDUCED BINDING SITE ON GPIIIA

[75] Inventors: Andrew L. Frelinger, III; Edward F. Plow; Mark H. Ginsberg, all of San Diego, Calif.

[73] Assignee: The Scripps Research Institute, La Jolla, Calif.

[21] Appl. No.: 417,565

[22] Filed: Oct. 5, 1989

Related U.S. Application Data

[63] Continuation-in-part of Ser. No. 175,342, Mar. 31, 1988, Pat. No. 5,114,842, which is a continuation-in-part of Ser. No. 70,953, Jul. 8, 1987, abandoned.

[51] Int. Cl.$^5$ .............................. G01N 33/567
[52] U.S. Cl. ..................... 435/7.21; 436/69; 436/504; 436/548; 436/811; 530/388.7
[58] Field of Search .................. 435/7.21, 7.92; 530/387, 388.7; 436/504, 548, 808, 811, 69

[56] References Cited

U.S. PATENT DOCUMENTS

| | | | |
|---|---|---|---|
| 4,427,646 | 1/1984 | Olexa et al. | 424/1.1 |
| 4,454,106 | 6/1984 | Gansow et al. | 424/1.1 |
| 4,544,640 | 10/1985 | Soma et al. | 436/506 |
| 5,114,842 | 5/1992 | Plow et al. | 424/85.8 |

OTHER PUBLICATIONS

Plow et al., Proc. Natl. Acad. Sci. USA 83: 6002-6006, 1986.
Pytela, et al., *Science 231:* 1559-62 (1986).
Nilsson, et al., Molecular *Immunol. 24:* 487-94 (1987).
Wakabayashi, et al., *J. Biol. Chem. 261:* 11097-11105 (1986).
Frelinger, et al., *J. Biol. Chem. 265:* 6346-6352 (1990).
Frelinger, et al., *Circulation 78:* 1231 (Abstract; 1988).
Frelinger, et al., *Clin. Res. 35(3):* 598A (Abstract; 1987).
Lam, et al., *J. Biol. Chem. 262:* 947-50 (1987).
Haber, in Monoclonal Antibodies and New Trends in Immunoassays, Bizollon (ed.), pp. 81-90, Elsevier Publishers (1984).
Bennett, et al., *PNAS USA 80:* 2417-2421 (1983).
Kohler, et al., *Nature 256:* 495-7 (1975).
Galfre, et al., *Meth. Enzymol. 73:* 3-46 (1981).
Lewis, et al., *Biochemistry 22:* 948-54 (1983).
Miles, et al., *Nature 219:* 186-9 (1968).
Wisdom, *Clin. Chem. 22:* 1243-1255 (1976).
Ginsberg, et al., *Chem. Abst. 106 (25):* 210580x (1986).
Matsueda, et al., *Chem. Abst. 108 (15):* 1281201 (1987).
Shani, et al., *Nucl. Med. Biol. 13:* 379-382 (1986).
Hynes, Cell 48: 549-554 (1987).
Chard, An Introduction to Radioimmunoassays and Related Techniques, Work & Work (eds), pp. 136-141 (1982).
Shadle, et al., *J. Cell Biol. 99:* 2056-60 (1984).
Ginsberg, et al., *J. Clin. Invest. 78:* 1103-1111 (1986).
Jemmerson, et al., *Science 232:* 1001-1004 (1986).
Jennings, et al., *Blood 65:* 1112-1119 (1985).
Charo, et al., *PNAS USA 83:* 8351-5355 (1986).
Varon, et al., *PNAS USA 80:* 6992-6995 (1983).
Poncz, et al., *J. Biol. Chem. 262:* 8476-8482 (1987).
Bray, et al., *J. Clin. Invest. 80:* 1812-1817 (1987).
Uzan, et al., *J. Biol. Chem. 171:* 87-93 (1988).

*Primary Examiner*—Esther L. Kepplinger
*Assistant Examiner*—Donna C. Wortman
*Attorney, Agent, or Firm*—Douglas A. Bingham; Thomas Fitting; April C. Logan

[57] ABSTRACT

An antibody that immunoreacts with a ligand-induced binding site (LIBS) on GPIIIa, and particularly, a LIBS induced in a platelet-associated GPIIb-IIIa/fibrinogen complex is disclosed. Further disclosed are diagnostic systems and methods for assaying LIBS-containing platelets in a vascular fluid sample using the antibodies of the invention.

12 Claims, 4 Drawing Sheets

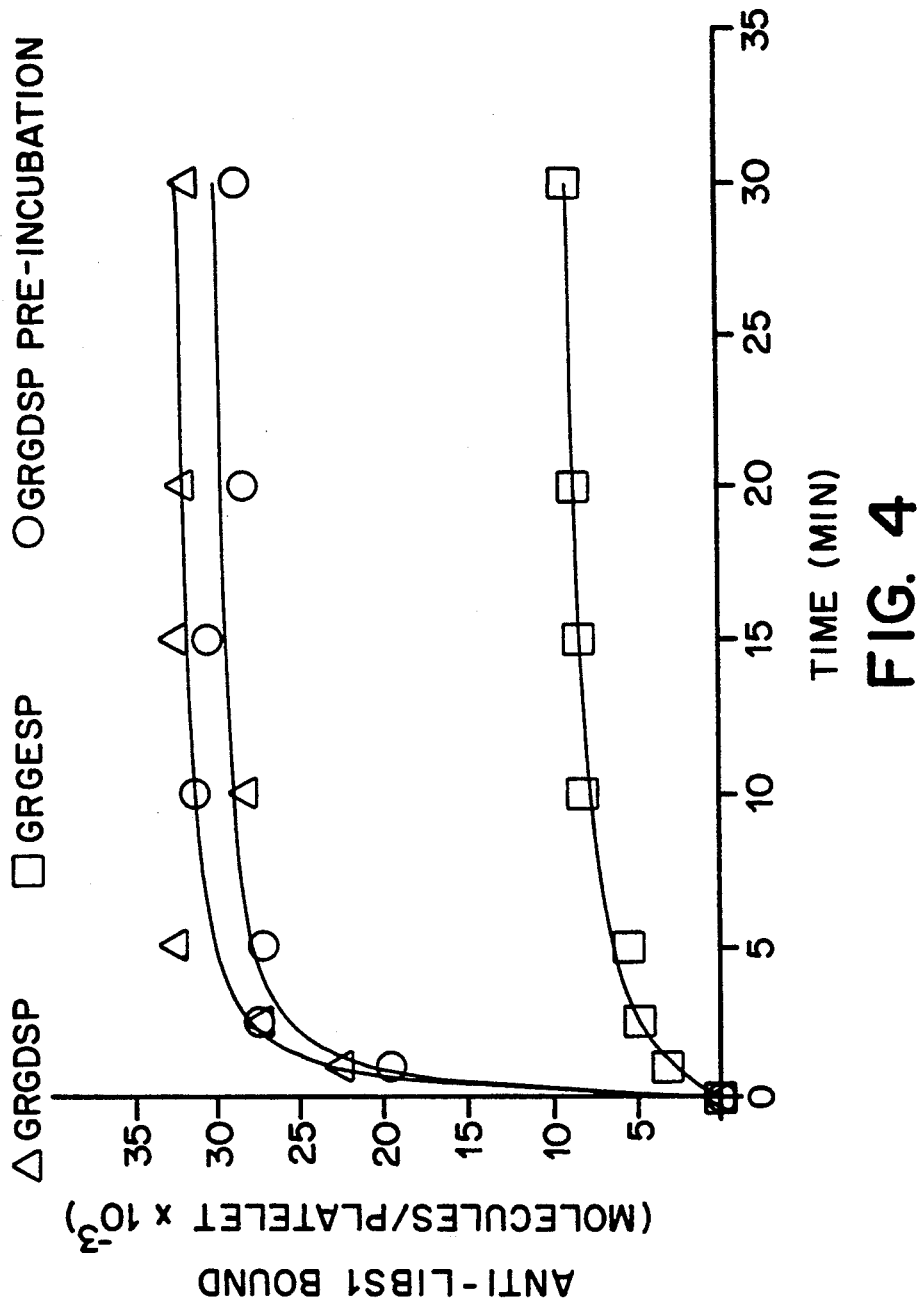

ANTIBODIES THAT BIND TO A LIGAND-INDUCED BINDING SITE ON GPIIIA

This invention was made with government support under National Institutes of Health Contracts HL-16411, HL-28235, and GM-37696. The Government has certain rights in the invention.

CROSS REFERENCE TO RELATED APPLICATION

This is a continuation-in-part application of copending application Ser. No. 175,342, filed Mar. 31, 1988, U.S. Pat. No. 5,114,842 which is a continuation-in-part application of copending application Ser. No. 070,953, filed Jul. 8, 1987, abandoned the disclosures of which are hereby incorporated by reference.

TECHNICAL FIELD

The present invention relates to antibodies that immunoreact with a GPIIIa antigenic determinant that is produced when a GPIIIa-containing receptor - specifically binds to a peptide, polypeptide or protein ligand. The present invention also relates to diagnostic methods to detect clotting disorders and thrombi.

BACKGROUND

Cell adhesion generally involves recognition of specific adhesive proteins by cell surface receptors. A family of cell surface receptors of particular interest to the present invention are the integrins.

According to Hynes, Cell, 48:549-554 (1987), integrins are a functionally and structurally related group of receptors that interact with a wide variety of ligands including extracellular matrix glycoproteins, complement and other cells. Integrins participate in cell-matrix and cell-cell adhesion in many physiologically important processes including embryological development, hemostasis, thrombosis, wound healing, immune and nonimmune defense mechanisms and oncogenic transformation. Two human genetic diseases, Glazmann's thrombasthenia and leukocyte adhesion deficiency, involve members of the integrin family.

Structurally, integrins are heterodimeric complexes comprised of noncovalently associated alpha and beta subunits. Within the integrin family there are recognized groups related by the presence of a similar beta subunit and members within each group are distinguished by unique alpha subunits.

For instance, GPIIb-IIIa is a noncovalent, $Ca^{++}$ dependent, heterodimer complex comprised of alpha and beta subunits. Jennings et al., J. Biol. Chem., 257:10458-10466 (1982). The alpha subunit, GPIIb consists of a heavy chain (hGPIIb) having a relative molecular weight of about 120 kilodaltons (KDa), and a light chain (1GPIIb) of about 20 KDa that are linked together by disulfide bonds. The beta subunit, GPIIIa is a single chain polypeptide of about 100 KDa. Phillips et al., J. Biol. Chem., 252:2121-2126 (1977). Cell surface molecules immunologically related to GPIIb-IIIa have been identified on a variety of cell types. See Thiagarajan et al., J. Clin. Invest., 75:896-901 (1985); Plow et al., Proc. Natl. Acad. Sci. USA, 83:6002-6006 (1986); and Fitzgerald et al., J. Biol. Chem., 260:10893-10896 (1985). GPIIb-IIIa contributes to platelet function through interactions with RGD-containing proteins such as fibrinogen [Bennett et al., Proc. Natl. Acad. Sci. USA, 80:2417-2421 (1983)], fibronectin [Ginsberg et al., J. Clin. Invest., 71:619-624 (1983)], and von Willebrand factor [Ruggeri et al., Proc. Natl. Acad. Sci. USA, 79:6038-6041 (1982)], and therefore is a component of the common platelet adhesive protein receptor [Pytela et al., Science, 231:1559-1562 (1986) and Plow et al., J. Biol. Chem., 259:5388-5391 (1984)].

Recent evidence indicates that GPIIb-IIIa is one of several adhesion receptors that share a similar beta subunit and the functional property of recognizing the tripeptide amino acid residue sequence Arg-Gly-Asp (using single letter symbols, RGD). Pytela et al., Science, 231:1559-1562 (1986) and Ruoslahti et al., Cell, 44:517-518 (1986). In addition to GPIIb-IIIa, this group of related receptors includes the vitronectin receptor (VnR) and fibronectin receptor (FnR) isolated from osteosarcoma cells [Pytela et al., Cell, 40:191-198 (1985), Pytela et al., Proc. Natl. Acad. Sci. USA, 82:5766-5770 (1985) and Sanchez-Madrid et al., J. Exo. Med., 158:1785-1803 (1983)].

The similar functional, structural, and antigenic properties of these proteins suggests GPIIb-IIIa and VnR (a GPIIIa-containing receptor) are members of an adhesion receptor group for which the designation "cytoadhesin" has been proposed. Plow et al., Proc. Natl. Acad. Sci. USA, 83:6002-6006 (1986). Within the cytoadhesin group, distinct alpha subunits combine with a common or very similar beta subunit, resulting in functionally distinguishable receptors. Ginsberg et al., J. Biol. Chem., 262:5437-5440 (1987).

At least two other groups of heterodimeric adhesion receptors have been identified in which a common beta subunit combines with a number of distinct alpha subunits. One group is found on leukocytes and has been referred to as the leukocyte adhesion family and includes LFA-1, Mac-1, and p150,95. Sanchez-Madrid et al., J. Exp. Med., 158:1785-1803 (1983) and Springer et al., Ciba. Found. Symp., 118:102-126 (1986). The other is more widely distributed and has been referred to as the VLA family Hemler et al., J. Biol. Chem., 262:3300-3309 (1987). The beta subunit of the VLA family [Hemler et al., J. Biol. Chem., 262:3300-3309 (1987)]in the chicken has been cloned and sequenced and designated "Integrin" [Tamkun et al., Cell, 46:271-282 (1986)]. The sequence of chicken integrin is similar to that of GPIIIa [Fitzgerald et al., J. Biol. Chem., 262:3936-3939 (1987)] and to the beta subunit of the leukocyte adhesion family [Kishimoto et al., Cell, 48:681-690 (1987)]. Moreover, partial sequences of several alpha subunits also indicate similarities. Ginsberg et al., J. Biol. Chem., 262:5437-5440 (1987); Suzuki et al., Proc. Natl. Acad. Sci. USA, 83:8614-8618 (1986); and Charo et al., Proc. Natl. Acad. Sci. USA, 83:8351-8356 (1986).

The sites on GPIIb-IIIa, or the other cytoadhesins, that are required for their functions as adhesion receptors are not well characterized. Several observations suggest that a functionally significant site on GPIIb-IIIa is near the epitope defined by the monoclonal antibody PMI-1. This antibody binds to the heavy chain of GPIIb [Shadle et al., J. Cell. Biol., 99:2056-2060 (1984)] and defines a region of GPIIb that is associated with several distinct- functional activities. First, PMI-1 inhibits adhesion of washed platelets to collagen. Shadle et al., J. Cell. Biol., 99:2056-2060 (1984). Second, the surface orientation of this region is regulated by divalent cations because millimolar (mM) concentrations of calcium or magnesium suppress expression of the PMI-1 epitope. Ginsberg et al., J. Clin. Invest., 78:1103-1111

(1986). Third, abnormal divalent cation regulation of the conformation of this site is associated with a functional thrombasthenic state. Ginsberg et al., *J. Clin. Invest.*, 78:1103-1111 (1986). Fourth, stimulation of platelets with up to 100 micromolar adenosine diphosphate (ADP) or epinephrine, 1 unit per milliliter thrombin, or 50 micrograms per milliliter calf skin collagen does not substantially increase the binding of PMI-1 antibodies to platelets.

Platelet activation has been reported to produce the appearance of antigenic sites on the platelet surface that are not present in the non-activated platelet, and at least one of such induced sites has been localized to the GPIIb-IIIa receptor complex. Shattil et al, *J. Biol. Chem.* 260:11107-11114 (1985); Coller, B.S., *J. Cell Biol.*, 103:451-456 (1986).

BRIEF SUMMARY OF THE INVENTION

It has now been found that cell surface receptors that have specifically bound a ligand can be distinguished from non-occupied receptors by the presence of a ligand-induced antibody binding site (LIBS). That is, a class of antigenic determinants has been discovered that are expressed when a cell surface receptor specifically binds a ligand. Those antigenic determinants are not expressed by either the non-occupied receptor or the non-bound ligand.

The present invention is directed to a method and diagnostic kit for the detection of the presence of a ligand-induced binding site in GPIIIa that is produced by the binding of a ligand molecule to a GPIIIa-containing receptor, and an antibody composition that is useful therein.

An antibody composition of the present invention is contemplated that contains a physiologically tolerable diluent together with an antibody molecule or fragment thereof that is capable of specifically immunoreacting with a ligand-induced binding site in GPIIIa when a GPIIIa-containing receptor is bound to a ligand but which does not immunoreact with either GPIIIa or the ligand when either is in a non-bound form. Preferably the antibody composition contains a monoclonal antibody or fragment thereof that specifically immunoreacts with a ligand-induced binding site in GPIIIa when GPIIb-IIIa is bound to an Arg-Gly-Asp-containing ligand (an RGD-containing ligand) such as fibrinogen.

In a particularly preferred embodiment, this antibody composition contains a monoclonal antibody or fragments thereof that are substantially similar to the antibody, or fragments of the antibody produced by hybridoma LIBS1.

The present invention contemplates a method of producing a monoclonal antibody that immunoreacts with a ligand-induced binding site on GPIIIa expressed by a receptor-ligand complex. This complex contains a cell surface receptor, such as GPIIb-IIIa, and a RGD-containing ligand that is specifically bound to the receptor. The method contemplated by the present invention comprises:

(a) immunizing a mammal with a composition containing the complex;

(b) removing antibody-producing cells from the immunized mammal and preparing a suspension of the cells;

(c) treating the cells with a transforming agent to produce transformed antibody-producing cells;

(d) cloning, by limiting dilution in a tissue culture medium that will not sustain non-transformed cells, the cells treated in step (c) to produce cloned transformants;

(e) assaying the tissue culture medium of the cloned transformants for the presence of secreted antibody molecules that immunoreact with the receptor-ligand complex but do not immunoreact with the cell surface receptor or the ligand when either is in non-bound form, thereby identifying a cloned transformant producing the antibody;

(f) growing the identified cloned transformant in a tissue culture medium under conditions for producing the secreted antibody molecules; and (g) harvesting the secreted antibody molecules from the culture medium of step (f).

In a preferred embodiment, the method of forming a monoclonal antibody that immunoreacts with a ligand-induced binding site on GPIIIa of the present invention contemplates:

(a) immunizing a mouse with a composition containing the receptor-ligand complex;

(b) removing the spleen from the mouse and preparing a suspension of the spleen cells;

(c) fusing the spleen cells with mouse myeloma cells in the presence of a fusion promoter to produce antibody-secreting hybridomas;

(d) diluting and culturing the individual fused cells into separate wells in a medium that will not sustain the unfused cells;

(e) assaying the supernatant in each well containing a hybridoma for the presence of secreted antibody molecules that immunoreact with the receptor-ligand complex but do not immunoreact with the cell surface receptor or the ligand when either is in non-bound form, thereby identifying a hybridoma producing the antibody;

(f) growing the identified hybridoma in a culture medium under conditions favoring secretion of the antibody molecules; and (g) harvesting the antibody molecules from the supernatant of the hybridoma.

In a particularly preferred embodiment, the method of the present invention contemplates transferring the identified hybridoma intraperitoneally into a second mouse and then harvesting the ascites or serum from this mouse, which ascites or serum contains the desired antibody.

The present invention additionally contemplates a method of detecting in vivo the presence of a receptor-ligand complex, as described above, that contains such a ligand-induced binding site on GPIIIa. This method comprises the steps of:

a) intravenously administering to a human subject an effective amount of a monoclonal antibody composition to produce an antibody concentration in the blood of about 0.1 to about 10 micromolar (uM), where this composition contains a physiologically tolerable diluent together with antibody molecules that immunoreact with the ligand-induced binding site (LIBS) in the receptor-ligand complex but do not immunoreact with the cell surface receptor or the ligand when either is in non-bound form, the antibody molecules being linked to an in vivo indicating means;

b) maintaining the administered subject for a predetermined time period sufficient for the antibody molecules to immunoreact with the LIBS in vivo and form an immunoreaction product; and c) assaying for the presence of any immunoreaction product formed in step (b) and thereby the presence of the complex in the subject.

Still further contemplated is a method of assaying for the presence of a receptor-ligand complex in a vascular fluid sample. The contemplated method comprises the steps of:

a) forming an immunoreaction admixture by admixing the vascular fluid sample with a monoclonal antibody composition as described above;

b) maintaining the admixture for a time period sufficient for the antibody molecules to immunoreact with the LIBS in any receptor-ligand complex present in the sample and form an immunoreaction product; and c) detecting the presence of any immunoreaction product formed in step (b) and thereby the presence of the complex in the sample.

In a preferred embodiment, this method is utilized to detect the presence of platelets expressing a GPIIb-IIIa-ligand complex in a vascular fluid sample.

Also contemplated is a method of detecting the presence of a thrombus in vivo comprising the steps of:

a) intravenously administering to a human subject an effective amount of a monoclonal antibody composition, as described above, to produce an antibody concentration in the blood of about 0.1 to about 10 uM, and preferably about 1.0 uM, in which the anti-LIBS antibody molecules in this composition are linked to an in vivo indicating means;

b) maintaining the administered subject for a predetermined time period sufficient for the antibody molecules to immunoreact with fibrinogen-bound platelets in vivo and form an immunoreaction product; and c) assaying for the presence of any immunoreaction product formed in step (b).

A diagnostic system in kit form is contemplated in the present invention. In one embodiment a diagnostic system for assaying for the presence of a receptor-ligand complex, as described above, in a vascular fluid sample is contemplated.

This system comprises:

a) a package containing, in an amount sufficient to perform at least one assay, a monoclonal antibody composition containing antibody molecules that immunoreact with a LIBS in said receptor-ligand complex but do not immunoreact with the cell surface receptor or the ligand when either is in non-bound form, and b) an indicating means or label.

In a second embodiment, a diagnostic system in kit form for assaying for the presence of such a cell receptor-ligand complex in vivo is contemplated, containing a package containing, in an amount sufficient to perform at least one assay, a physiologically administrable monoclonal antibody composition, as described above, in which the antibody molecules are linked to an in vivo indicating means. In a preferred embodiment, a kit for assaying for the presence of a thrombus in vivo is contemplated in which the antibody molecules immunoreact with a LIBS on GPIIIa in a thrombus, such as the LIBS on GPIIIa in a platelet GPIIb-IIIa-ligand complex.

In a preferred embodiment, the antibody composition contains an anti-LIBS antibody (anti-LIBS1) that immunoreacts with GPIIIa in GPIIb-IIIa-ligand complex, thereby providing a kit for assaying a vascular fluid sample for the presence of platelets containing a GPIIb-IIIa-ligand complex.

Also contemplated is a method of inhibiting clot contraction in vitro that results when the GPIIIa-containing receptor is occupied by either fibrinogen or RGD-containing peptides. In this method a monoclonal antibody is utilized that can immunoreact with a ligand-induced binding site (LIBS1) expressed on GPIIIa by a GPIIb-IIIA receptor-ligand complex, as described above. This method comprises:

a) admixing a monoclonal antibody with a blood clot sample containing a GPIIIa-containing receptor-ligand complex; and b) maintaining the admixture under biological assay conditions for a time period sufficient for the monoclonal antibody present to immunoreact with any ligand-induced binding sites expressed on GPIIIa in the GPIIIa-containing receptor-ligand complex.

Further contemplated is a method of inhibiting clot contraction in vivo comprising the steps of:

(a) intravenously administering to a mammal an effective amount of a monoclonal antibody composition, as described above, and preferably containing anti-LIBSI antibody molecules that are capable of immunoreacting with a ligand-induced binding site (LIBSl) expressed on GPIIIa when GPIIb-IIIa is bound to a RGD-containing ligand to form a LIBS1-expressing receptor-ligand complex;

(b) maintaining the administered mammal for a time period sufficient for the antibody molecules to immunoreact with any LIBS1-expressing receptor-ligand complex in vivo and form an immunoreaction product that substantially inhibits the contraction of blood clots containing this immunoreaction product.

BRIEF DESCRIPTION OF THE DRAWINGS

In the Figures forming a portion of the disclosure of this invention:

FIG. 4 illustrates the time course of anti-LIBS1 binding to platelets as described in Example 7. Platelets were incubated in Tyrode's buffer with 1 mM GRGDSP (circles) or GRGESP (squares) for 15 min before adding anti-LIBSI Ig (0.2 uM) (time zero), and the amount of bound antibody determined at varied times. In a separate incubation, 1 mM GRGDSP and antibody were both added at time zero (triangles). Preincubation and binding were at room temperature. Results shown are averages of triplicate determinations.

DETAILED DESCRIPTION OF THE INVENTION

A. Definitions

Figure 1:
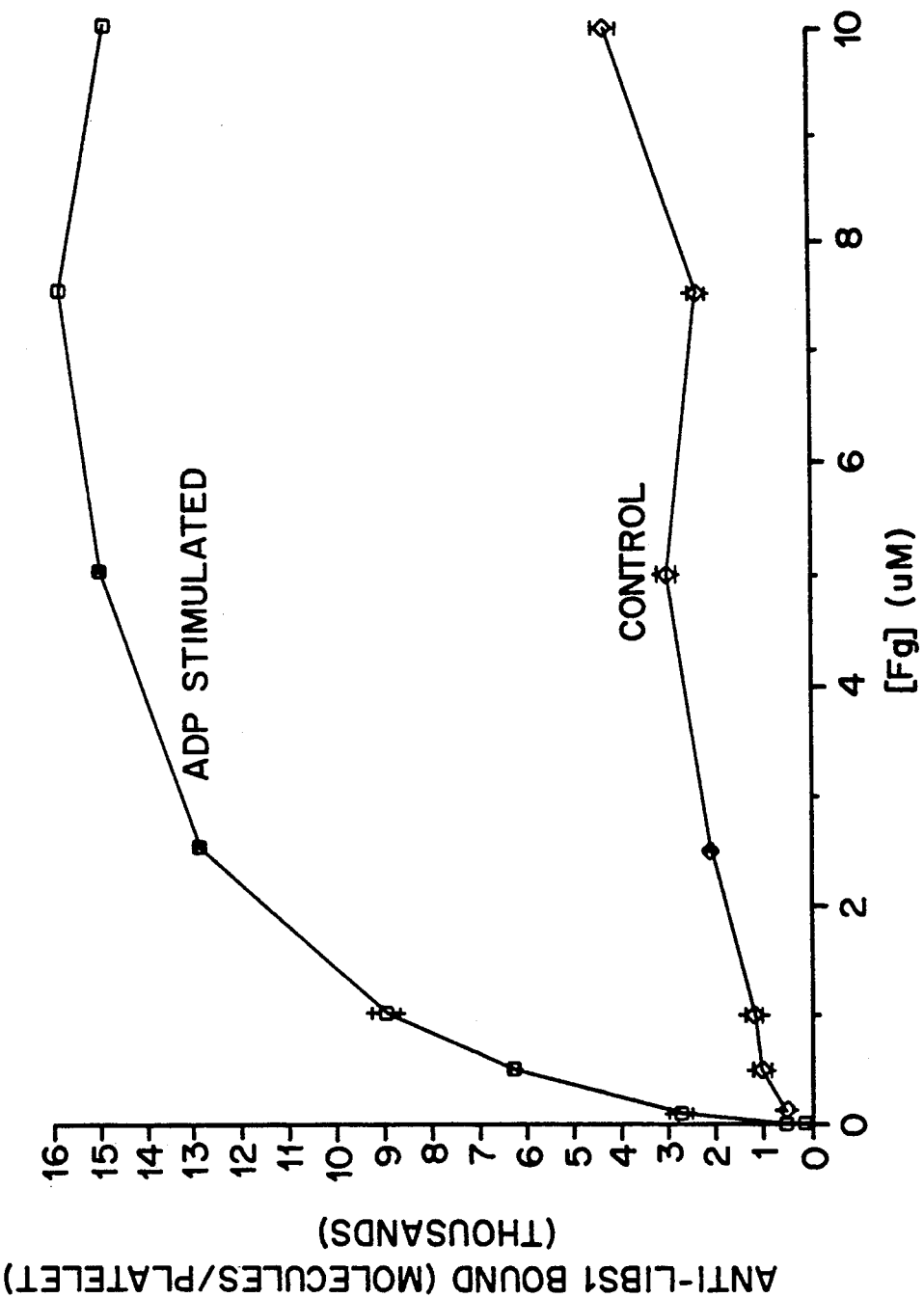
FIG. 1 illustrates anti-LIBS1 binding to platelets in the presence of ADP-stimulated fibrinogen as described in Example 4. Gel-filtered platelets ($1 \times 10^8$ platelets/ml) were incubated with $^{125}$I-labeled anti-LIBS1 and varied concentrations of fibrinogen in the presence (ADP-stimulated) or absence (Control) of ADP (10 uM) for 30 min at 37° C. Platelet-bound radioactivity was separated from free by centrifuging the platelets through a layer of sucrose. Results are shown as the average of triplicate determinations +/− one standard deviation.

Amino Acid: All amino acid residues identified herein are in the natural L-configuration. In keeping with standard polypeptide nomenclature, *J. Biol. Chem.*, 243:3557-59, (1969), abbreviations for amino acid residues are as shown in the following Table of Correspondence:

| TABLE OF CORRESPONDENCE SYMBOL | | |
|---|---|---|
| 1-Letter | 3-Letter | AMINO ACID |
| Y | Tyr | L-tyrosine |
| G | Gly | glycine |
| F | Phe | L-phenylalanine |
| M | Met | L-methionine |
| A | Ala | L-alanine |
| S | Ser | L-serine |
| I | Ile | L-isoleucine |
| L | Leu | L-leucine |
| T | Thr | L-threonine |
| V | Val | L-valine |
| P | Pro | L-proline |
| K | Lys | L-lysine |
| H | His | L-histidine |
| Q | Gln | L-glutamine |
| E | Glu | L-glutamic acid |
| W | Trp | L-tryptophan |
| R | Arg | L-arginine |
| D | Asp | L-aspartic acid |
| N | Asn | L-asparagine |
| C | Cys | L-cysteine |

It should be noted that all amino acid residue sequences are represented herein by formulae whose left to right orientation is in the conventional direction of amino-terminus to carbosy-terminus. Furthermore, it should be noted that a dash at the beginning or end of an amino acid residue sequence indicates a bond to a further sequence of one or more amino acid residues up to a total of about fifty residues in the polypeptide chain.

Polypeptide and Peptide: Polypeptide and peptide are terms used interchangeably herein to designate a linear series of no more than about 50 amino acid residues connected one to the other by peptide bonds between the alpha-amino and carboxy groups of adjacent residues.

Protein: Protein is a term used herein to designate a linear series of greater than 50 amino acid residues connected one to the other as in a polypeptide.

Receptor: Receptor and receptor protein are terms used herein to indicate a biologically active proteinaceous molecule that specifically binds to (or with) other molecules.

Ligand and Coqnate Ligand: Ligand refers to a molecule that contains a structural portion that is bound by specific interaction with a particular receptor protein.

Ligand-induced Bindino Site (LIBS): A LIBS is a neo-antigenic determinant that is expressed by a cell surface receptor-ligand complex that is produced by a non-random (specific) binding reaction but is not expressed by either the non-occupied receptor or the non-bound ligand. A LIBS can be either "conformational" or "sequential". A LIBS as used herein can be the result of specific alterations of the receptor induced by ligand binding, i.e., a "cryptic antigenic determinant", or it can be formed by a combination of receptor and ligand amino acid residues at a receptor-ligand contact site.

Cryotic Antigenic Determinant: Refers to a neo-antigenio determinant formed by changes in conformation or membrane-surface orientation of a receptor protein upon non-random binding to its cognate (specific) ligand. The receptor proteins described herein do not normally express a cryptic antigenic determinant unless the receptor has specifically bound a ligand.

B. Antibodies and Antibody Compositions

1. Antibody Compositions

The term "antibody" in its various grammatical forms is used herein to refer to immunoglobulin molecules and immunologically active portions of immunoglobulin molecules, i.e., molecules that contain an antibody combining site or paratope. Illustrative antibody molecules are intact immunoglobulin molecules, substantially intact immunoglobulin molecules and those portions of an immunoglobulin molecule that contain the paratope, including those portions known in the art as Fab, Fab', F(ab')$_2$ and F(v).

The term "antibody combining site" refers to that structural portion of an antibody molecule comprised of a heavy and light chain variable and hypervariable regions that specifically binds (immunoreacts with) antigen. The term "immunoreact" in its various forms is used herein to refer to binding between an antigenic determinant-containing molecule and a molecule containing an antibody combining site such as a whole antibody molecule or a portion thereof.

The term "antigenic determinant" refers to the actual structural portion of the antigen that is immunologically bound by an antibody combining site. The term is also used interchangeably with "epitope".

The term "physiologically administerable composition" as used herein refers to solutions, suspensions and mixtures that are capable of being readily provided into the body of a mammal by parenteral, oral or rectal administration and includes injectable solutions, emulsions and the like.

As used herein, the term "specifically bound" refers to a non-random binding reaction between a cell surface receptor and a ligand molecule. Illustrative of a specifically-bound receptor-ligand complex is that between platelet GPIIb-IIIa and fibrinogen at the platelet surface. Other ligands known to specifically bind GPIIb-IIIa and express a LIBS on the receptor-ligand complex includes the polypeptide GRGDSP, the gamma chain polypeptide from amino acid residue 400 to 411 of fibrinogen, and the like.

An antibody composition of the present invention is characterized as containing antibody molecules that immunoreact with a LIBS that is expressed upon the binding of a ligand. In a preferred embodiment, the antibody molecules immunoreact with a LIBS on GPIIIa that is expressed by a GPIIIa-containing receptor, such as GPIIb-IIIa or vitronectin receptor, upon binding to its specific ligand, such as fibrinogen. In another preferred embodiment, an antibody composition of this invention contains more than one species of paratope capable of immunoreacting with a LIBS on GPIIIa.

An antibody composition of the present invention, containing anti-LIBS antibody molecules that immunoreact with platelet-associated GPIIb-IIIa/fibrinogen complexes but do not substantially immunoreact with either GPIIb-IIIa or fibrinogen when unbound, is capable of distinguishing fibrinogen-bound platelets from platelets that have not bound fibrinogen. Thus, preferred antibody compositions are those containing antibody molecules that immunoreact with LIBS, and particularly with LIBS1, on GPIIIa when present in a platelet-associated GPIIb-IIIa/fibrinogen complex.

A contemplated antibody composition is typically produced by immunizing a mammal with an inoculum containing a complex of a specific ligand non-randomly (specifically) bound to a GPIIa-containing cellular receptor, such as GPIIb-IIIa, thereby inducing in the mmal antibody molecules having the appropriate immunospecificity for a LIBS present on the complex. The antibody molecules are then collected from the mammal and isolated to the extent desired by well known techniques such as, for example, by immunoaffinity chromatography. The antibody composition so produced can be used inter alia, in the diagnostic methods and systems of the present invention to detect fibrinogen-bound platelets in a body sample.

2. Monoclonal Antibody Compositions

An anti-LIBS monoclonal antibody composition is also contemplated by the present invention. The phrase "monoclonal antibody composition" in its various grammatical forms refers to a population of antibody molecules that contain only one species of antibody combining site capable of immunoreacting with a particular antigen. A monoclonal antibody composition thus typically displays a single binding affinity for any antigen with which it immunoreacts. A monoclonal antibody composition may therefore contain an antibody molecule having a plurality of antibody combining sites, each immunospecific for a different antigen, e.g., a bispecific monoclonal antibody.

A monoclonal antibody composition is typically composed of antibodies produced by clones of a single cell called a hybridoma that secretes (produces) but one kind of antibody molecule. The hybridoma cell is formed by fusing an antibody-producing cell and a myeloma or other self-perpetuating cell line. Such antibodies were first described by Kohler and Milstein, *Nature* 256:495–497 (1975), which description is incorporated by reference.

A monoclonal antibody composition can also be produced by methods well known to those skilled in the art of producing chimeric antibodies. Those methods include isolating, manipulating, and expressing the nucleic acid that codes for all or part of an immunoglobulin variable region including both the portion of the variable region comprised by the variable region of immunoglobulin light chain and the portion of the variable region comprised by the variable region of immunoglobulin heavy chain. Methods for isolating, manipulating, and expressing the variable region coding nucleic acid in procaryotic and eucaryotic hosts are disclosed in Robinson et al., PCT Publication No. WO 89/0099; Winter et al., European Patent Publication No. 0239400; Reading, U.S. Pat. No. 4,714,681; Cabilly et al., European Patent Publication No. 0125023; Sorge et al., *Mol. Cell Biol.*, 4:1730–1737 (1984); Beher et al., *Science*, 240:1041–1043 (1988); Skerra et al., *Science*, 240:1030–1041 (1988); and Orlandi et al., *Proc. Natl. Acad. Sci., U.S.A.*, 86:3833–3837 (1989). Typically the nucleic acid codes for all or part of an immunoglobulin variable region that binds a preselected antigen (ligand). Sources of such nucleic acid are well known to one skilled in the art and, for example, may be obtained from a hybridoma producing a monoclonal antibody that binds the preselected antigen, or the preselected antigen may be used to screen an expression library coding for a plurality of immunoglobulin variable regions, thus isolating the nucleic acid.

A monoclonal antibody composition of the present invention is characterized as containing antibody molecules that immunoreact with a LIBS expressed by a cell surface receptor-ligand complex, preferably a cryptic antigenic determinant induced in the GPIIb-IIIa complex and more preferably a LIBS present on GPIIIa.

The antibody molecules contained in these preferred monoclonal antibody compositions immunoreact with GPIIIa present in a receptor-ligand complex and can immunologically react with platelet-associated GPIIb-IIIa when it has bound fibrinogen but do not inhibit the binding of fibrinogen by platelet-associated GPIIb-IIIa. Representative monoclonal antibody compositions of this type are those described in Example 2 and Table 1. Particularly preferred is a monoclonal antibody composition that comprises antibody molecules that immunoreact with the specific LIBS present on GPIIIa in a GPIIb-IIIa-fibrinogen complex designated LIBS1, and more preferably are those that are produced by the hybridoma LIBSa.

3. Methods for Producing Monoclonal Antibody Compositions

The present invention contemplates a method of forming a monoclonal antibody molecule that (a) immunoreacts with a ligand-induced binding site (LIBS) expressed by a cell surface receptor-ligand complex, and (b) does not immunoreact with either the nonoccupied receptor or the non-bound ligand of the receptor-ligand complex. The method comprises the steps of:

(a) Immunizing an animal with a cell surface-receptor-ligand complex. Preferably, the immunogen is a complex of GPIIb-IIIa and a GPIIb-IIIa specific ligand, such as fibrinogen, GRGDSP, the fibrinogen gamma chain, and the like. The immunization is typically accomplished by administering the complex to an immunologically competent mammal an immunologically effective amount, i.e., an amount sufficient to produce an immune response. Preferably, the mammal is a rodent such as a rabbit, rat or mouse. The mammal is then maintained for a time period sufficient for the mammal to produce cells secreting antibody molecules that immunoreact with the receptor-ligand complex.

(b) A suspension of antibody-producing cells removed from the immunized mammal is then prepared. This is typically accomplished by removing the spleen of the mammal and mechanically separating the individual spleen cells in a physiologically tolerable medium using methods well known in the art.

(c) The suspended antibody-producing cells are treated with a transforming agent capable of producing a transformed ("immortalized") cell line. Transforming agents and their use to produce immortalized cell lines are well known in the art and include DNA viruses such as Epstein Barr Virus (EBV), Simian Virus 40 (SV40), Polyoma Virus and the like, RNA viruses such as Moloney Murine Leukemia Virus (MoMuLV), Rous Sarcoma Virus and the like, myeloma cells such as P3X63-Ag8.653, Sp2/O-Ag14 and the like.

In preferred embodiments, treatment with the transforming agent results in the production of a hybridoma by means of fusing the suspended spleen cells with mouse myeloma cells from a suitable cell line by the use of a suitable fusion promoter. The preferred ratio is about 5 spleen cells per myeloma cell in a suspension containing about $10^8$ splenocytes. A preferred fusion promoter is polyethylene glycol having an average molecule weight from about 1000 to about 4000 (commercially available as PEG 1000, etc.); however, other fusion promoters known in the art maybe employed.

The cell line used should preferably be of the so-called "drug resistant" type, so that unfused myeloma cells will not survive in a selective medium, while hybrids will survive. The most common class is 8-azaguanine resistant cell lines, which lack the enzyme hypoxanthine-guanine phosphoribosyl transferase and hence will not be supported by HAT (hypoxanthine, aminopterin, and thymidine) medium. It is also generally preferred that the myeloma cell line used be of the so-called "non-secreting" type which does not itself produce any antibody. In certain cases, however, secreting myeloma lines may be preferred.

(d) The transformed cells are then cloned, preferably to monoclonality. The cloning is preferably performed in a tissue culture medium that will not sustain (support) non-transformed cells. When the transformed cells are hybridomas, this is typically performed by diluting and culturing in separate containers the mixture of unfused spleen cells, unfused myeloma cells, and fused cells (hybridomas) in a selective medium which will not sustain the unfused myeloma cells. The cells are cultured in this medium for a time sufficient to allow death of the unfused cells (about one week). The dilution can be a limiting dilution, in which the volume of diluent is statistically calculated to isolate a certain number of cells (e.g., 1-4) in each separate container (e.g., each well of a microtiter plate). The medium is one (e.g., HAT medium) that will not sustain the drug-resistant (e.g., 8-azaguanine resistant) unfused myeloma cell line.

(e) The tissue culture medium of the cloned transformants is analyzed (or assayed) to detect the presence of secreted anti-LIBS antibody molecules using well known immunological techniques. Preferably, the medium is monitored for the presence of anti-GPIIb-IIIa LIBS antibody molecules, and more preferably anti-GPIIIa LIBS antibody molecules.

(f) A desired transformant is then selected and grown in an appropriate tissue culture medium for a suitable length of time, followed by recovery (harvesting) of the desired antibody from the culture supernatant by well known techniques. The suitable medium and suitable length of culturing time are also well known or are readily determined.

Representative and preferred methods for producing anti-LIBS monoclonal antibody compositions are described in Example 2.

To produce a much greater concentration of slightly less pure monoclonal antibody, the desired hybridoma can be transferred by injection into mice, preferably syngeneic or semisyngeneic mice. The hybridoma will cause formation of antibody-producing tumors after a suitable incubation time, which will result in a high concentration of the desired antibody (about 5-20 mg/ml) in the bloodstream and peritoneal exudate (ascites) of the host mouse.

Media and animals useful for the preparation of these compositions are both well known in the art and commercially available and include synthetic culture media, inbred mice and the like. An exemplary synthetic medium is Dulbecco's minimal essential medium [DMEM; Dulbecco et al., Virol. 8:396 (1959)]supplemented with 4.5 gm/l glucose, 20 mM glutamine, and 20% fetal calf serum. An exemplary inbred mouse strain is the Balb/c.

The monoclonal antibody compositions produced by the above method can be used, for example, in diagnostic and therapeutic modalities wherein formation of a LIBS-containing immunoreaction product is desired, such as a GPIIIa-containing immunoreaction product.

C. Hybridomas

Hybridomas of the present invention are those which are characterized as having the capacity to produce an anti-LIBS monoclonal antibody composition.

A preferred hybridoma of the present invention is characterized as producing antibody molecules that immunoreact with a cell surface receptor cryptic antigenic determinant, preferably with a LIBS present on GPIIIa, and more preferably with a LIBS on GPIIIa in a platelet-associated GPIIb-IIIa-fibrinogen complex.

Representative preferred hybridomas are prepared and described in Example 2. Particularly preferred is the hybridoma culture designated LIBSa.

Hybridoma culture LIBSa has been deposited pursuant to Budapest Treaty requirements with the American Type Culture Collection (ATCC), Rockville, Md. 20852, U.S.A., on May 17, 1989, and was assigned accession number HB 10150.

This hybridoma was deposited in a depository affording permanence of the deposit and ready accessibility thereto by the public upon the grant of a patent, under conditions which assure that access to the hybridoma will be available during the pending of the patent application to those entitled to such access, and that all restrictions on the availability to the public of the hybridoma as deposited will be irrevocably removed upon the granting of the patent. The deposited hybridoma will be maintained by the ATCC, and all maintenance fees have been paid, for the term of the patent or 30 years from the date of deposit, whichever is longer, and in all events for at least five years after the date of the last request for access.

Methods for producing hybridomas producing (secreting) antibody molecules having a desired immunospecificity, i.e., having the ability to immunoreact with a particular protein, an identifiable epitope on a particular protein and/or a polypeptide, are well known in the art and are described further herein. Particularly applicable is the hybridoma technology described by Niman et al., Proc. Natl. Acad. Sci. USA, 80:4949-4953 (1983), and by Galfre et al., Meth. Enzymol., 73:3-46 (1981), which descriptions are incorporated herein by reference.

D. Therapeutic Methods and Compositions

Therapeutic methods and compositions are contemplated for inhibiting the contraction of blood clots. When this method is carried out in vitro, a blood clot-containing sample is admixed with an antibody composition containing antibody molecules that immunoreact with a LIBS on GPIIIa in a GPIIb-IIIa receptor-ligand complex and the admixture is maintained under biological conditions compatible with the formation of an immunoreaction product for a time period sufficient for the antibody to immunoreact with any expressed LIBS on GPIIIa in the receptor-ligand complex. In a preferred embodiment, the antibody composition used in this method contains antibody molecules that immunoreact with LIBSI on GPIIIa in a GPIIb-IIIa-fibrinogen complex.

When this method is carried out in vivo, an effective amount of an antibody composition containing a physiologically tolerable diluent and antibody molecules that immunoreact with a LIBS on GPIIIa in a GPIIb-IIIa receptor-ligand complex is intravenously administered to a mammal, and the mammal is maintained for a sufficient time period to allow the antibody molecules to immunoreact with any LIBS-expressing receptor-ligand complex present and form an immunoreaction product. In preferred embodiments the antibody composition contains antibody molecules that immunoreact with LIBSI on GPIIIa in a GPIIb-IIafibrinogen complex.

As used herein, the terms "pharmaceutically acceptable," "physiologically tolerable" and its grammatical variations, as they refer to compositions, carriers, diluents and reagents, are used interchangeably and represent that the materials are capable of administration to or upon a mammal without the production of untowards physiological effects such as nausea, dizziness, gastric upset and the like.

Preferably, for both the in vitro and in vivo methods, the antibody molecules are present as a monoclonal antibody composition and more preferably are those produced by the hybridoma LIBSa.

The antibody molecule-containing compositions administered can take the form of solutions or suspensions.

The preparation of a therapeutic composition that contains antibody molecules as active ingredients is well understood in the art. Typically, such compositions are prepared as injectables, either as liquid solutions or suspensions, however, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient as are well known. Suitable excipients are, for example, water, saline, dextrose, glycerol, ethanol, or the like and combinations thereof. In addition, if desired, the composition can contain minor amounts of auxiliary substances such as wetting or emulsifying agents, pH buffering agents and the like which enhance the effectiveness of the active ingredient.

An antibody molecule composition can be formulated into a therapeutic composition in a neutralized pharmaceutically acceptable salt form. Pharmaceutically acceptable salts include the acid addition salts (formed with the free amino groups of the antibody molecule) that are formed with inorganic acids such as, for example, hydrochloric or phosphoric acids, or such organic acids as acetic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The therapeutic antibody molecule-containing compositions are conventionally administered intravenously, as by injection of a unit dose, for example. The term "unit dose" when used in reference to a therapeutic composition of the present invention refers to physically discrete units suitable as unitary dosages for humans, each unit containing a predetermined quantity of active material calculated to produce the desired therapeutic effect in association with the required diluent, i.e., carrier, or vehicle.

The compositions are administered in a manner compatible with the dosage formulation, and in a therapeutically effective amount. The quantity to be administered depends on the subject to be treated, and capacity of the subject to utilize the active ingredient. Precise amounts of active ingredient required to be administered depend on the judgment of the practitioner and are peculiar to each individual. However, suitable dosage ranges are of the order of one to several milligrams of active ingredient per individual per day and depend on the route of administration. Suitable regimens for initial administration and booster shots are also variable, but are typified by an initial administration followed by repeated doses at one or more hour intervals, by a subsequent injection or other administration. Alternatively, continuous intravenous infusion sufficient to maintain therapeutically effective concentrations in the blood are contemplated. Therapeutically effective blood concentrations of antibody molecules of the present invention are in the range of about 0.1 uM to about 10 uM, preferably 1.0 uM.

E. Diagnostic Systems

A diagnostic system in kit form of the present invention includes, in an amount sufficient for at least one assay, a composition containing antibody or monoclonal antibody molecules or fragments thereof of the present invention, as a separately packaged reagent, together with a label that indicates the presence of an immunoreaction product. Instructions for use of the packaged reagent are also typically included.

"Instructions for use" typically include a tangible expression describing the reagent concentration or at least one assay method parameter such as the relative amounts of reagent and sample to be admixed, maintenance time periods for reagent/sample admixtures, temperature, buffer conditions and the like.

In one embodiment, a diagnostic system is contemplated for assaying for the presence of a receptor-ligand complex, preferably fibrinogen-bound platelets, in a complex-containing vascular fluid sample, such as blood or plasma. The diagnostic system comprises a package containing antibody molecules that immunoreact with a LIBS present on said receptor-ligand complex but do not immunoreact with the cell surface receptor or the ligand when either is in non-bound form, i.e., when not present in a complex. Preferably, the antibody molecules immunoreact with a LIBS present on GPIIIa and more preferably immunoreact with a LIBS on GPIIIa in fibrinogen-associated platelets containing a GPIIb-IIIa-ligand complex. Further preferred are kits wherein the antibody molecules are linked to a radionuclide label, preferably $^{125}$I-labeled antibody molecules.

In another embodiment, a diagnostic system of the present invention is useful for assaying for the presence of a thrombus in vivo. The system comprises a package containing antibody molecules that immunoreact with a LIBS present on a GPIIb-IIIa-ligand complex. The antibody molecules are linked to an in vivo indicating means. Preferably, the antibody molecules are present as a monoclonal antibody composition consisting essentially of antibody molecules that immunoreact with a LIBS on GPIIIa expressed in response to the binding of a GPIIb-IIIa specific ligand to GPIIb-IIIa on the platelets.

For both an in vitro and in vivo embodiment, a diagnostic system of the present invention includes a label or indicating means capable of signaling the formation of a specifically bound complex containing an antibody molecule of the present invention.

As used herein, the terms "label" and "indicating means" in their various grammatical forms refer to single atoms and molecules that are either directly or indirectly involved in the production of a detectable signal to indicate the presence of a complex. "In vivo" labels or indicating means are those useful within the body of a human subject and include $^{111}$In, $^{99}$Tc, $^{67}$Ga, $^{186}$Re, and $^{132}$I. Any label or indicating means can be linked to or incorporated in an antibody molecule that is part of an antibody or monoclonal antibody composition of the present invention, or used separately, and those atoms or molecules can be used alone or in conjunction with additional reagents. Such labels are themselves well-known in clinical diagnostic chemistry and constitute a part of this invention only insofar as they are utilized with otherwise novel methods and/or systems.

The linking of labels, i.e., labeling of, polypeptides and proteins is well known in the art. For instance, antibody molecules produced by a hybridoma can be labeled by metabolic incorporation of radioisotope-containing amino acids provided as a component in the culture medium. See, for example, Galfre et al., *Meth. Enzymol.*, 73:3–46 (1981). The techniques of protein conjugation or coupling through activated functional groups are particularly applicable. See, for example, Aurameas, et al., *Scand. J. Immunol.*, Vol. 8, Suppl. 7:7–23 (1978), Rodwell et al., *Biotech.*, 3:889–894 (1984), and U.S. Pat. No. 4,493,795.

The diagnostic systems can also include, preferably as a separate package, a specific binding agent. A "specific binding agent" is a molecular entity capable of selectively binding a reagent species of the present invention but is not itself an antibody molecule of the present invention. Exemplary specific binding agents are antibody molecules, complement proteins or fragments thereof, protein A and the like. Preferably, the specific binding agent can bind the antibody molecule of this invention when it is present as part of a complex.

In preferred embodiments the specific binding agent is labeled. However, when the diagnostic system includes a specific binding agent that is not labeled, the agent is typically used as an amplifying means or reagent. In these embodiments, the labeled specific binding agent is capable of specifically binding the amplifying means when the amplifying means is bound to a reagent species-containing complex.

The diagnostic kits of the present invention can be used in an "ELISA" format to detect, for example, the presence or quantity of fibrinogen-bound platelets in a body fluid sample such as serum, plasma or urine "ELISA" refers to an enzyme-linked immunoasorbent assay that employs an antibody or antigen bound to a solid phase and an enzyme-antigen or enzyme-antibody conjugate to detect and quantify the amount of an antigen or antibody present in a sample. A description of the ELISA technique is found in Chapter 22 of the 4th Edition of *Basic and Clinical Immunology* by D.P. Sites et al., published by Lange Medical Publications of Los Altos, Calif. in 1982 and in U.S. Pat. Nos. 3,654,090; No. 3,850,752; and No. 4,016,043, which are all incorporated herein by reference.

Thus, in preferred embodiments, the antibody or antigen reagent component can be affixed to a solid matrix to form a solid support that is separately packaged in the subject diagnostic systems.

The reagent is typically affixed to the solid matrix by adsorption from an aqueous medium, although other modes of affixation, well known to those skilled in the art, can be used.

Useful solid matrices are well known in the art. Such materials include the cross-linked dextran available under the trademark SEPHADEX from Pharmacia Fine Chemicals (Piscataway, N.J.); agarose; polystyrene beads about 1 micron to about 5 millimeters in diameter available from Abbott Laboratories of North Chicago, Ill.; polyvinyl chloride, polystyrene, cross-linked polyacrylamide, nitrocellulose- or nylon-based webs such as sheets, strips or paddles; or tubes, plates or the wells of a microtiter plate such as those made from polystyrene or polyvinylchloride.

The reagent species, labeled specific binding agent or amplifying reagent of any diagnostic system described herein can be provided in solution, as a liquid dispersion or as a substantially dry power, e.g., in lyophilized form. Where the indicating means is an enzyme, the enzyme's substrate can also be provided in a separate package of a system. A solid support such as the before-described microtiter plate and one or more buffers can also be included as separately packaged elements in this diagnostic assay system.

The packages discussed herein in relation to diagnostic systems are those customarily utilized in diagnostic systems. Such packages include glass and plastic (e.g., polyethylene, polypropylene and polycarbonate) bottles, vials, plastic and plastic-foil laminated envelopes and the like.

F. Assay Methods

The present invention contemplates any method that results in detecting a LIBS on a cell surface receptor-ligand complex and preferably a LIBS which is expressed in response to the binding of a GPIIb-IIIa specific ligand to GPIIb-IIIa. Particularly preferred is the detection of a LIBS present on the GPIIIa subunit of a GPIIIa-containing cell surface receptor-ligand complex, such as the GPIIb-IIIa complex containing fibrinogen bound thereto as is found in a thrombus or in fibrinogen-bound platelets.

The method for detecting a LIBS comprises the formation of an immunoreaction product between a LIBS and an anti-LIBS antibody molecule, as disclosed herein, and the subsequent detection of the immunoreaction product so formed. The LIBS to be detected can be present in a vascular fluid sample, such as a blood sample containing platelets, or can be present in a body tissue, such as a thrombus in vivo. Those skilled in the art will understand that there are numerous well known clinical diagnostic chemistry procedures that can be utilized to form detectible immunocomplexes. Thus, while exemplary assay methods are described herein, the invention is not so limited.

1. Thrombus Detection

A method is contemplated for detecting in vivo in a human subject the presence of a LIBS on a receptor-ligand complex, such as is found on a GPIIIa-containing receptor-ligand complex present on a thrombus. An effective amount of an antibody composition or a monoclonal antibody composition of the present invention containing anti-LIBS antibody molecules, linked to an in vivo indicating means, is intravenously administered into the subject in the form of a physiologically tolerable preparation. In preferred embodiments the labeled antibody molecules are those that immunoreact with LIBS on GPIIIa in GPIIb-IIIa but not with unbound GPIIb-IIIa, and more preferably are those antibody molecules produced by hybridoma LIBSa.

An effective amount of an antibody composition for in vivo detection of a LIBS is an amount sufficient to deliver and produce a blood concentration of anti-LIBS antibody molecules of about 0.1 to about 10 mM.

The subject is then maintained for a predetermined time period sufficient for the labeled antibody molecules to react with the LIBS present as part of a thrombus and form a complex, and preferably for an additional time period sufficient for a substantial amount of any non-reacted antibody molecules to clear the body. The subject is then assayed for the presence and preferably location of any labeled complex that formed.

2. Detection of Fibrinogen-Bound Platelets in a Body Sample

Various heterogeneous and homogeneous assay protocols can be employed, either competitive or noncompetitive for detecting the presence and preferably amount of fibrinogen-bound platelets in a platelet-containing body sample, preferably a body fluid sample, more preferably a vascular fluid sample such as blood or a platelet-containing portion of blood. The method involves the admixture of a platelet-containing blood sample with antibody molecules that immunoreact with a LIBS on GPIIb-IIIa, and preferably with a LIBS on GPIIIa in GPIIb-IIIa but not with unbound GPIIb-IIIa. For example, a heparin-preserved (non-clotted) blood sample and $^{125}$I-labeled anti-LIBS1 antibody molecules are admixed. The immunoreaction admixture thus formed is maintained under biological assay conditions for a time period sufficient for any fibrinogen-bound platelets to immunoreact with the labeled antibodies and form a labeled immunoreaction product. The labeled immunoreaction products are then separated from the non-reacted labeled-antibodies, typically by centrifugation sufficient to pellet all platelets present in the sample. The amount of labeled immunoreaction product formed is then assayed.

Biological assay conditions are those that maintain the biological activity of the antibody molecules and polypeptide molecules of this invention and the fibrinogen-bound platelets sought to be assayed. Those conditions include a temperature range of about 40° C. degrees C (4 C) to about 45° C., preferably about 37° C., at a pH value range of about 5 to about 9, preferably about 7, and an ionic strength varying from that of distilled water to that of about one molar sodium chloride, preferably about that of physiological saline. Methods for optimizing such conditions are well known in the art.

Insofar as various drugs, such as the synthetic peptide GRGDSP or the snake venom peptide trigramin, can be used to modulate platelet function by complexing GPIIb-IIIa via the binding site for RGD-containing ligands, the present invention also contemplates methods to detect the degree of occupancy of the ligand binding site by the drug on GPIIb-IIIa. The method is practiced essentially as described above for detecting fibrinogen-bound platelets, except that an RGD-containing ligand analog, and not fibrinogen, has bound the platelets. The method is practiced to quantitate the amount of analog (drug) bound, i.e., the degree of occupancy of the RGD-ligand binding site.

3. Diaonostic Method for the Detection of Clotting Disorders

The ability of platelets to bind fibrinogen and/or to express a LIBS, preferably a LIBS on GPIIIa such as LIBS1, can be monitored in a diagnostic method of the present invention. A platelet-containing body fluid sample is admixed and incubated with a GPIIb-IIIa specific ligand such as fibrinogen or a synthetic peptide such as GRGDSP, or with other GPIIb-IIIa specific ligands such as the fibrinogen gamma chain polypeptide (Fb gamma 400–411), for a time period sufficient for the ligand to bind to and form a complex with GPIIb-IIIa-containing receptor on the platelet surface. The amount of ligand admixed is an amount sufficient to saturate the GPIIb-IIIa specific LIBS present on the platelets in the body sample. The formation of the GPIIb-IIIa complex results in the expression of LIBS on GPIIIa in normal platelets.

An anti-LIBS antibody composition of the present invention is then added to the mixture and maintained for a time period sufficient for the anti-LIBS antibody molecules to immunoreact with the expressed LIBS antigenic determinant. The amount of LIBS present is then determined by use of an indicating means. In preferred embodiments, the antibody composition contains antibody molecules that immunoreact with LIBS1, and more preferably contains the antibody molecules produced by hybridoma LIBSa. In the case of LIBS1, a significant variation in the amount of LIBS1 per platelet from the approximately 35,000 sites/platelet of normal platelets is indicative of a clotting disorder. A decrease in LIBS1/platelet of greater than 50% amount suggests a thrombasthenic condition.

The following examples are intended to illustrate, but not limit, the present invention.

EXAMPLE 1

Isolation of GPIIb-IIIa

A. Platelet Isolation

Sixty milliliters (ml) of whole human blood was collected in 5 ml of ACD (0.065 M citric acid, 0.085 M sodium citrate, 2% dextrose) containing hirudin (Sigma Chemical Co., St. Louis, MO) at a final concentration of 0.06 units per milliliter (U/ml) and centrifuged for 15 minutes at 120×g. The resulting supernatant, designated platelet rich plasma (PRP), was recovered, isolated and further centrifuged for 15 minutes at 1200×g to form a pellet of isolated platelets. The supernatant formed is collected and used as platelet-poor plasma in other assays.

B. GPIIb-IIIa Isolation from Platelets

A platelet pellet prepared as in Example 1A, was resuspended in 5 ml TBS (0.15 M NaCl, 0.2 M Tris, pH 7.4, 0.5 mM CaCl$_2$, 0.01 mM leupeptin) and sonicated on ice for 10 minutes at a maximum setting using a Model W-375 sonicator (Heat Systems Ultrasonics, Plainview, N.Y.). The sonicated suspension was twice frozen and thawed using a dry ice-methanol ice bath and stored at minus 20° C. The frozen-thawed platelet sonicate was layered on top of 5 ml of a sucrose solution (40% v/v in TBS), and centrifuged at 4° C. for one hour at 38,000 rotations per minute (RPM) in a SW41 centrifuge rotor (Beckman Instruments, Fullerton, Calif.) to form a milky colored infranatant. The milky-infranatant was then recovered and centrifuged at 43,000 RPM in a SW50.1 centrifuge rotor (Beckman) at 4° C. for one hour. The resulting pellet was resuspended in typically 1-2 ml TBS to form a platelet membrane solution, the protein concentration of which was determined to be in the range of 10-25 mg/ml, using the Bio-Rad Protein Assay Kit (Bio-Rad, Richmond, Calif.) according to the manufacturer's instructions.

The platelet membrane solution was again centrifuged in a SW50.1 centrifuge rotor as above and the resulting pellet was resuspended in 2 ml of extraction buffer (0.03 M Tris, pH 7.4, 0.01 mM leupeptin, 200 mM n-octyl-beta-D-glucopyranoside; Calbiochem-Behring, La Jolla, Calif.). The platelet membrane extract thus formed was admixed thoroughly by vortexing and then maintained at room temperature for 30 minutes. The extract was thereafter centrifuged at 45,000 RPM in a SW50.1 centrifuge rotor for 1 hour at 4° C. and the platelet membrane extract supernatant thus formed was recovered.

The recovered supernatant was applied to a LKB Ultrogel Aca 34 gel filtration column (3×97 cm, LKB Instruments, Gaithersburg, Md.) that had been equilibrated with 1 liter of column buffer (0.03 M Tris, pH 7.4, 0.1 mM $CaCl_2$, 0.1% n-octyl-beta-D-glucopyranoside) and 5 ml fractions were collected from the resulting column effluent. The optical density at 280 nanometers of each fraction was determined and fractions around the several peaks were combined to form a pool for each peak. Samples from each pool were analyzed by electrophoresis in 6% polyacrylamide slab gels using the reducing buffers and procedures described by Laemmli, Nature (London), 227:680–685 (1970), and low molecular weight protein standards ranging in size from 14.4 kilodaltons (KDa) to 92.5 KDa (Bio-Rad, Richmond, Calif.). The pool containing predominantly two protein species having molecular weights corresponding to GPIIb and GPIIIa, i.e., 120 KDa and 100 KDa, respectively was recovered. The protein concentration of the isolated GPIIb-IIIa preparation thus prepared was typically determined using the Bio-Rad Protein Assay Kits to be in the range of 0.3 to 0.8 mg/ml.

C. Polypeptide Affinity Isolation of GPIIb-IIIa

Synthesis of peptide of the formula Gly-Arg-Gly-Asp-Ser-Pro-Lys was accomplished using the technique of Merrifield, J. Am. Chem. Soc., 85:2149–54 (1963) or purchased from Peninsula Laboratories (Belmont, Calif.). All peptides were greater than 90% homogenous when analyzed by high performance liquid chromatography (HPLC) utilizing a $C_{18}$ bondapak column and a 0–60% linear gradient of acetonitrile in 0.1% trifluoroacetic acid. Affinity matrices containing the immobilized peptide Gly-Arg-Gly-Asp-Ser-Pro-Lys were prepared by coupling the peptide to cyanogen bromide-activated Sepharose 4B (Pharmacia P-L Biochemicals, Piscataway, N.J.) according to the manufacturer's instructions. The affinity matrix containing the immobilized peptide was packed into columns (0.7×15 cm) and equilibrated with PBS at pH 7.5 containing 50 mM octylglucoside, 1 mM phenylmethanesulfonylfluoride (PMSF), 1 mM $CaCl_2$ and 1 mM $MgClz$ at 4° C.

The platelet membrane extract supernatant prepared according to Example 1B was applied to the affinity matrix containing Gly-Arg-Gly-Asp-Ser-Pro-Lys. The unbound proteins were eluted with 100 ml of PBS at pH 7.5, containing 25 mM octylglucoside, 1 mM PMSF, 1 mM $CaCl_2$, and 1 mM $MgCl_2$ (column buffer). Bound GPIIb-IIIa was then eluted by washing the column with 10 ml of column buffer containing the designated peptide at a concentration of 1.7 mM followed by another 10 ml of column buffer. Fractions of 2.5 ml each were collected, and the proteins in each fraction were analyzed by polyacrylamide gels (7.5%) after reduction with 10% 2-mercaptoethanol. The protein bands were visualized by staining with Coomassie Blue according to the methods described in *Current Protocols in Molecular Biology*, Ausubel et al., eds., John Wiley and Sons, New York, 1987.

D. Immunoaffinity Isolation of GPIIb-IIIa

An immunoaffinity column was prepared by coupling the antibody PMI-1 (which binds to GPIIb, ATCC, Rockville, Md.) to Affi-Gel 10 (Biorad, Richmond, Calif.) at 4 mg of antibody per ml of resin using the instructions provided by the manufacturer of the activated resin. Platelets prepared according to Example 1A ($6 \times 10^{10}$) were lysed in 1 ml of 50 mM octylglucoside in a column buffer consisting of 10 mM N-[2-hydroxyethIl]piperazine-N-[2'ethanesulfonic acid]- (HEPES), 1 mM $CaCl_2$, 1 mM $MgCl_2$, $0.15$ M NaCl, 1 mg/ml phenylmethanesulfonylfluoride (PMSF), 1.25 mg/ml N-ethyl-maleimide and 0.1 mg/ml leupeptin. The insoluble material was removed by centrifugation at 45,000 RPM in an SW 50.1 rotor for one hour at 4° C. The supernatant, designated as platelet lysate, was collected, the peptide Gly-Arg-Gly-Asp-Ser-Pro (GRGDSP) was admixed at 1 mM, and thereafter admixed with 2 ml of antibody-Affi-Gel 10 and maintained for 12 to 18 hours at 4° C. This admixture was then placed into a column and washed with 10 column volumes of column buffer containing 1 mM of the peptide Gly-Arg-Gly-Asp-Ser-Pro and 25 mM octylglucoside, and eluted with five column volumes of column buffer at pH 5 containing 25 mM octylglucoside and no peptide. The eluted fractions were immediately neutralized to pH 7.2, pooled and dialyzed against column buffer containing 5 mM octylglucoside. The protein concentration of the isolated GPIIb-IIIa preparation thus prepared was determined using the Bio-Rad Protein Assay Kit.

EXAMPLE 2

Preparation of Monoclonal Antibody Compositions

Monoclonal antibodies that immunoreact with a ligand-induced binding site on GPIIb-IIIa were produced using standard hybridoma technology with exceptions as noted. Briefly, two Balb/c mice were each immunized intraperitoneally four times at one week intervals with increasing doses (1 ug, 10 ug, 25 ug, 50 ug and 100 ug, respectively) of immunogen consisting of the receptor-ligand complex comprised of affinity-isolated GPIIb-IIIa, as prepared in Example 1C (1.25 mg/ml) and peptide Gly-Arg-Gly-Asp-Ser-Pro at 3 mg/ml. The immunogen was diluted 1:1 in Complete Freund's Adjuvant for the first immunization, in Incomplete Freund's Adjuvant for the second and third immunization, and in normal saline for the fourth. Three days after the fourth immunization about $1 \times 10^8$ lymphocytes were isolated from the spleens of both mice, admixed into a suspension and fused with $5 \times 10^7$ P3X63AG8.053 mouse myeloma cells using 50% PEG 1500 as the cell fusion promoter. The resulting transformed (fused) antibody-producing cells (hybridomas) were initially transferred to 96-well microtiter plates at a density of about $1 \times 10^6$ cells per well and cultured in selective HAT media.

Tissue culture supernatants from about 2000 wells appearing to contain viable HAT resistant hybridoma cells after 8 days of culturing were screened in the ELISA assay described in Example 3A for the presence of antibody molecules that immunoreact with GPIIb-IIIa. About 44 hybridoma cultures were identified that produced GPIIb-IIIa-immunoreacting antibody molecules. The isolated hybridomas were then subcloned twice at limiting dilutions to provide about 1 cell per well and 24 of the resultant hybridoma cultures were shown to be of monoclonal origin on the basis of three criteria: (1) each supernatant was from a single cell foci and immunoreacted with GPIIb-IIIa in the ELISA screen, (2) each supernatant showed a single homogeneous band when analyzed by cellulose acetate gel electrophoresis according to the method described in *Monoclonal Antibodies: Principles and Practice*, J. W. Goding, ed., Academic Press, Inc., Orlando, Fla., 1983, and (3) each supernatant contained a single isotype of immunoglobulin when analyzed using the Mouse Ig Screening and Isotyping Kit according to the instructions provided by the manufacturer, Boehringer-Mannheim Biochemicals, Indianapolis, Ind. Results of the isotype analysis of the hybridoma supernatants are shown in Table 1.

TABLE 1

GRGDSP Modulation Of LIBS Epitope Expression
In ELISAs To Identify Anti-LIBS Monoclonal Antibody

| Mab | Subunit[a] Specificity | Isotype | B/B$_0$[b] − | + | % Decrease[c] |
|---|---|---|---|---|---|
| LIBSa | GPIIIa | G$_1$K | 0.61 | 0.32 | 48 |
| LIBSb | GPIIIa | G$_{2a}$K | 0.62 | 0.35 | 44 |
| LIBSc | GPIIIa | G$_1$K | 0.45 | 0.21 | 53 |
| LIBSd | GPIIIa | G$_{2b}$K | 0.79 | 0.62 | 22 |
| LIBSe | GPIIIa | G$_1$K | 0.82 | 0.52 | 37 |
| LIBSf | GPIIIa | ND[d] | 0.29 | 0.17 | 41 |
| LIBSg | GPIIIa | ND | 0.64 | 0.51 | 20 |
| LIBSh | GPIIIa | G$_{2a}$K | 0.38 | 0.28 | 26 |
| LIBSi | GPIIIa | G$_{2a}$K | 0.22 | 0.17 | 23 |
| PMI-2[e] | GPIIIa | G$_{2a}$K | 0.58 | 0.46 | 21 |
| Mab15 | GPIIIa | G$_1$K | 0.25 | 0.23 | 8 |
| Mab19 | GPIIIa | MK | 0.32 | 0.32 | 0 |
| Mab23 | GPIIIa | G$_{2a}$K | 0.17 | 0.15 | 12 |
| LIBSj | hGPIIb | MK | 0.90 | 0.70 | 22 |
| PMI-1[e] | hGpIIb | G$_{2b}$K | 0.98 | 0.36 | 63 |
| Mab13 | hGPIIb | G1K | 0.61 | 0.51 | 16 |
| Mab10 | hGPIIb | G$_1$K | 0.84 | 0.79 | 6 |
| Mab18 | lGPIIb | MK | 0.40 | 0.34 | 15 |
| Mab16 | lGPIIb | MK | 0.54 | 0.47 | 13 |
| Mab5 | lGPIIb | MK | 0.66 | 0.64 | 3 |
| LIBSk | | G$_1$K | 0.80 | 0.59 | 26 |
| Mab38 | | G$_1$K | 0.82 | 0.69 | 16 |
| Mab51 | | ND | 0.76 | 0.73 | 4 |
| LIBSm | | ML | 0.39 | 0.54 | −38 |

[a]Subunit specificity was determined by Western blotting as described in Example 2.
[b]Ratio of the A490 in the presence (B) of platelet lysate (equivalent to $5 \times 10^8$ platelets/ml) to the A490 in the absence (B$_0$) of lysate. The ratio B/B$_0$ was measured both in the presence (+) of GRGDSP (1 mM) and in the absence (−) of GRGDSP.
[c]A change in B/B$_0$ upon addition of GRGDSP indicates the presence of a LIBS. Antibodies were considered to be anti-LIBS if the percent change in B/B$_0$ was greater than 20%.
[d]ND = Not determined.
[e]PMI-1 and PMI-2 were generated in a separate immunization and fusion.

The above screening procedure resulted in the identification of 22 hybridomas that produce antibody molecules that immunoreact with plasticimmobilized GPIIb-IIIa.

To identify hybridomas that produce antibody molecules that immunoreact with a ligand-induced binding site (LIBS) on GPIIb-IIIa (i.e., a GPIIb-IIIa LIBS), a competition ELISA screen was conducted as described in Example 3B discussed hereinafter, in which the immunoreaction admixture was maintained in the presence and absence of a GPIIb-IIIa specific ligand to express a GPIIb-IIIa LIBS. Anti-GPIIb-IIIa LIBS antibody molecules are those that exhibit a change in the ratio of the absorbance at 490 nm (B/B$_0$) of greater than 20% when measured in the presence (as compared to the absence) of GPIIb-IIIa specific ligand. Twelve hybridomas were identified that produce antibody molecules that immunoreact with GPIIb-IIIa LIBS, and the hybridomas are designated herein as LIBSa-LIBSm, as shown in Table 1.

In addition, it is seen that other anti-LIBS antibody molecules have been isolated by the disclosed methods, as shown in Table 1, that immunoreact with other LIBS epitopes present on the GPIIb or GPIIIa subunits of the platelet receptor.

The locations of the particular GPIIb-IIIa LIBS detected by the monoclonal antibodies shown in Table 1 were mapped to subunit regions of the platelet receptor by western immunoblotting according to the general methods described by Tobwin et al., *Proc. Natl. Acad. Sci U.S.A*, 76:4350-54, (1979). Briefly, GPIIb-IIIa isolated in Example 1B was subjected to electrophoresis on 7.5% SDS polyacrylamide gels (SDS-PAGE) under reducing conditions, transferred to a membrane and immunoreacted with supernatants of the hybridomas shown in Table 1. The immunoreaction products formed between the monoclonal antibodies provided in the hybridoma supernatants and the GPIIb-IIIa protein subunits on the membranes were detected using biotinylated second antibody and avidin-conjugated peroxidase according to manufacturer's instructions (Vectastain ABC Method, Vector Laboratories, Burlingame, Calif.).

The results of the Western immunoblot mapping showed that most of the hybridoma supernatants contained antibody molecules that immunoreacted with a protein having an apparent molecular weight on SDS-PAGE PAGE of 120 kilodaltons (KDa), 20 KDa or 100 KDa, corresponding to GPIIb heavy chain (hGPIIb), GPIIb light chain (lGPIIb) or GPIIIa, respectively. In a few cases, the antibody molecules did not react with any of the isolated GPIIb-IIIa subunits, leaving their subunit specificity uncharacterized. The determined subunit specificities are shown in Table 1.

Thus it is seen that the monoclonal antibody molecule produced by hybridoma LIBSa, which antibody molecule is also referred to herein as LIBSa, immunoreacts with the GPIIIa subunit of the GPIIb-IIIa platelet receptor. In addition the LIBSa antibody molecule immunoreacts with the LIBSI epitope present on a receptor-ligand complex comprised of GPIIb-IIIa and a GPIIb-IIIa specific ligand.

Monoclonal antibody compositions comprised of isolated antibody molecules were also prepared by isolating the antibody molecules from the ascites fluid of a mouse containing one of the hybridoma cell lines shown in Table 1 using protein A-Sepharose typically obtained from Pharmacia Inc. (Piscataway, N.J.) and used according to manufacturer's instructions.

The protein concentration of isolated antibody molecule compositions as needed was determined using the Bio-Rad Protein Assay Kit (Bio-Rad, Richmond, Calif.) according to the manufacturer's instructions.

To prepare a monoclonal antibody composition containing $^{125}$I-labeled antibody molecules, 350 microliters (ul) of PBS (0.15 M NaCl, 0.01 M sodium phosphate, pH 7.09) containing 1 milligram per milliliter (mg/ml) of the above isolated antibody molecules were admixed with 40 micrograms (ug) of chloramine-T and 1 milliCurie (mCi) of carrier-free Na$^{125}$I (Amersham, Arlington Heights, Ill.). The resulting admixture was maintained for 5 minutes at about 20° C. and then admixed with 20 ul of a 2 mg/ml sodium metabisulfite solution (2 mg/ml) and 20 ul of a potassium iodide solution. Thereafter, 800 ul of PBS containing 1% BSA were admixed followed by further admixture of diisopropylfluorophosphate to a final concentration of 10 mM. The resulting admixture was maintained for 60 minutes at 22° C. and then dialyzed against PBS. The specific activity of the resulting $^{125}$I-labeled antibody molecules was about 4.5 microCurie (uCi) per ug.

Compositions containing Fab fragments from the above isolated antibody molecules were prepared by digestion with papain (200:1 weight per weight of Ig to papain) for 6 hours at 37° C. following the methods of Mage et al., *Methods in Enzymology*, 70:142-150 (1980). Undigested Ig and Fc fragments were removed by chromatography on protein A-Sepharose. The resulting Fab fragments-containing compositions were then ready for use, or were $^{125}$I-labeled, as needed, using the same procedures as described above for monoclonal antibody compositions.

EXAMPLE 3

ELISA Assays

A. ELISA To Screen Monoclonal Antibodies

Antibody molecules contained in hybridoma culture supernatants were examined for their ability to immunoreact with GPIIb-IIIa. Fifty microliters (ul) of coating solution (0.M NaHCO$_3$, pH 8.0, 0.1% NaN$_3$) containing 10 ug/ml of isolated GPIIb-IIIa prepared in Example 1B were admixed into the wells of flat-bottom 96-well microtiter plates (Immulon 2; Dynatech Laboratories, Chantilly, Va.). The plates were then maintained for 60 minutes at 37° C. to permit the GPIIb-IIIa to adsorb onto the walls of the wells. The coating solution was removed by shaking, the wells were rinsed twice with washing buffer (10 mM Tris at pH 7.4, 0.05% (v/v) TWEEN-20, 0.15M NaCl, and 200 mg/ml merthiolate), and 200 ul of blocking solution [5% bovine serum albumin (BSA;w/v) in coating solution]- were admixed into each well (solid support) to block excess protein sites.

The wells were maintained for 60 minutes at about 37° C. and then the blocking solution was removed. About 50 ul of hybridoma culture supernatant diluted 1:1 in dilution buffer consisting of 0.1% (w/v) BSA in washing buffer was added to each well to form an immunoreaction admixture. The resulting solid/liquid phase immunoreaction admixtures were maintained at room temperature for 60 minutes to permit formation of a first solid phase-bound immunoreaction product between the solid phase-bound GPIIb-IIIa-ligand complex and admixed antibodies. The solid and liquid phases were then separated, the wells were rinsed twice with washing buffer, and excess liquid was removed by shaking.

Fifty ul of a solution containing horseradish peroxidase labeled goat anti-mouse IgG (Tago Inc., Burlingame, Calif.), diluted 1:1000 in dilution buffer was admixed into each well to form a second solid/liquid phase immunoreaction admixture (labeling immunoreaction admixture). The wells were maintained for 60 minutes at room temperature to permit formation of a second immunoreaction product between the labeled antibody and any solid phase-bound antibody of the first immunoreaction product and then rinsed twice with washing buffer to isolate the solid phase-bound label-containing immunoreaction products. Excess liquid was then removed from the wells.

Fifty ul of freshly prepared chromogenic substrate solution containing 4.0 mg/ml 0-phenylenediamine and 0.012% (v/v) hydrogen peroxide in CP buffer (243 ml of 0.1M citric acid and 250 ml of 0.2M dibasic sodium phosphate per liter H$_2$O, pH 5.0) were then admixed into each well to form a color developing-reaction admixture. After maintaining the color developing-reaction admixture for 10 minutes at about 20° C., 50 ul of 2 N H$_2$SO$_4$ were admixed into each well to stop the developing-reaction, and the resulting solutions were assayed for absorbance at 490 nanometers (nm) light wavelength using a Model 310 ELISA plate reader (Bio-Tek Instruments, Winooski, Vt.).

Antibody molecule compositions were considered to contain anti-GPIIb-IIIa immunoreactive antibody molecules if the measured absorbance at 490 nm (A490) was at least 6 times above background i.e., above about 0.3 optical density units when measured at A490.

B. Competition ELISA To Detect Anti-LIBS Antibodies

Antibody molecules contained in antibody compositions were examined for their ability to immunoreact with GPIIb-IIIa LIBS in a competition ELISA conducted similarly to the ELISA described in Example 3A with the following exceptions as noted.

Before an antibody composition was added to a GPIIb-IIIa coated microtiter wells, 20 ul of ELISA assay buffer consisting of 10 mM TRIS-HCl at pH 7.4, 0.15M NaCl, 0.05% (v/v) TWEEN-20, 0.02% (w/v) sodium merthiolate, 5 mM CaCl$_2$, 5 mM MgCl2 and 0.1% (w/v) BSA was added to each microtiter well. Then 10 ul of a solution containing platelet lysate at $2 \times 10$; platelets per ml, prepared as in Example 1D, was added to one set of wells and platelet lysate was omitted from a second set of wells. To both sets, with or without platelet lysate, was added 10 ul of a second solution that contained either 0 or 5 mM of the RGD-containing polypeptide ligand GRGDSP in ELISA assay buffer. Thereafter, 10 ul of an antibody composition at 0.3 μg/ml was added to both sets of wells at an antibody concentration diluted in ELISA assay buffer so as to be the limiting component in the ELISA immunoreaction admixture. Antibody concentrations are present as a limiting component when it has been diluted in ELISA assay buffer to produce an optical density at A490 of about 1.0 when measured using the ELISA assay of Example 3A with the exception that ELISA assay buffer is used in place of dilution buffer.

The results obtained in each immunoreaction admixture were measured for the presence of a developed color reaction as before. Absorbance measured in wells that contained no platelet lysate is referred to as B$_0$, and the absorbance measured in wells that contained platelet lysate is referred to as B. A ratio of absorbance is calculated for B/B$_0$, and expressed as measured either in the presence (+) or absence (−) of RGD-containing ligand (GRGDSP). The expression of a LIBS cryptic antigenic determinant is determined by calculating the percentage decrease observed in B/B$_0$ when ligand is added to the GPIIb-IIIa contained in platelet lysate in the immunoreaction admixture. A decrease upon addition of ligand in B/B$_0$ that exceeds 20% indicates an antibody molecule that immunoreacts with a LIBS epitope. Table 1 shows the results of Competition ELISA for monoclonal antibody molecules prepared in Example 2 that immunoreact with GPIIb-IIIa.

EXAMPLE 4

Expression of the GPIIIa Cryptic Determinant by Fibrinogen-Bound Platelets

Platelet rich plasma (PRP) was prepared as in Example 1A and divided into 2 aliquots. In one aliquot, the platelets were stimulated to express functional GPIIb-IIIa (fibrinogen receptors) by admixture of adenosine diphosphate (ADP) to a 10 uM final concentration to produce ADP-stimulated platelets. As a negative control, the second aliquot of PRP received no stimulus to produce non-stimulated platelets.

$^{125}$I-labeled LIBSa (anti-LIBS1) Fab fragments, prepared by usual techniques from the $^{125}$I-labeled antibodies described in Example 2, were then admixed to a 0.8 uM final concentration with several samples of each of the PRP aliquots in the presence of varying concentrations of fibrinogen. The immunoreaction admixtures thus formed were maintained at 37° C. for 30 minutes to permit formation of labeled immunoreaction products, i.e., fibrinogen-bound platelet/$^{125}$I-anti-LIBS1 complexes. The label-containing immunoreaction products were then separated from unbound $^{125}$I-anti-LIBS1 by centrifugation of the platelets through a sucrose cushion of 0.3 ml of 20% sucrose in a Beckman Microfuge B (Beckman Instruments, Inc., Fullerton, Calif.) to form a platelet pellet. The amount of $^{125}$I-anti LIBS1 associated with the pellet was then determined by gamma counting.

FIG. 1 illustrates the results of this study, and demonstrates that anti-LIBS1 antibody molecules immunoreact with stimulated, fibrinogen-bound, platelets but do not substantially immunoreact with non-stimulated platelets. It is believed that the $^{125}$I-anti-LIBS1 observed as "bound" in the non-stimulated PRP aliquot was due to non-specific binding ("sticking") and/or the presence of a naturally occurring background level of stimulated, fibrinogen-bound platelets or platelets stimulated and bound as a result of handling. The concentration of fibrinogen required for a half-maximal increase in anti-LIBS1 binding was about 0.7 uM, which is approximately the K$_d$ for fibrinogen binding to platelets. These results therefore indicate that binding of fibrinogen, an Arg-Gly-Asp (RGD) amino acid residue sequence-containing ligand, by the GPIIb-IIIa cytoadhesin results in expression of an otherwise cryptic antigenic determinant. Thus, anti-LIBS1 antibody molecules, and antibody molecules of similar immunospecificity, can be used to assay for the presence and amount of stimulated, fibrinogen-bound platelets in a vascular fluid sample.

EXAMPLE 5

Expression of GPIIb-IIIa Cryptic Antigenic Determinants By Ligand Binding

A. Assay for Antibodt Binding to Platelets That Express Cryptic Antigenic Determinants by Admixture Washed platelets were isolated as described in Example 1A, and were resuspended in 2 ml of calcium-free Tyrode's buffer (0.13M NaCl, 0.0026M KCl, 0.002M MgCl$_2$. 6H$_2$O, 5 mM Hepes, 0.012M NaHCO$_3$, pH 7.2) which was first treated by admixture with Chelex 100 (200–400 mesh sodium form, Bio-Rad Laboratories, Richmond, Calif.), maintained to complex any divalent cations present in the Tyrode's buffer and filtered to remove the complexed divalent cations from the buffer. The platelet suspension was then applied to a Sepharose CL2B column (40 ml total bed volume, Pharmacia, Inc., Piscataway, N.J.) equilibrated with the same Tyrode's buffer. The platelets were recovered in the void volume of the column in 4 to 5 ml. The washed platelets were then resuspended to a concentration of $1 \times 10^8$ per ml in the same Tyrode's buffer. The above-prepared washed platelet containing solution was than divided into aliquots. Monoclonal antibody compositions containing various concentrations of $^{125}$I-labeled LIBSa (anti-LIBS1) antibody molecules in Tyrode's buffer prepared as described in Example 2, were admixed first with 1) polypeptide GRGESP (0.8 mM), 2) polypeptide GRGDSP (0.8 mM) or 3) polypeptide GRGDSP (0.8 mM) plus ADP (10 mM). The $^{125}$I-labeled antibody/peptide admixtures were then admixed with the platelet aliquots containing about $1 \times 10^8$ a platelets/ml. The resulting immunoreaction admixtures were then maintained for 30 min at 37° C. to permit expression of the cryptic antigenic determinant and to allow the formation of $^{125}$I-labeled immunoreaction products, i.e., ligand-bound platelet/$^{125}$I-antibody complexes. The label containing immunoreaction products were then separated from non-bound $^{125}$I-labeled antibody by centrifugation of the platelet aliquot through a sucrose cushion as described in Example 4, and the platelet-associated radioactivity was determined as before.

Figure 2:
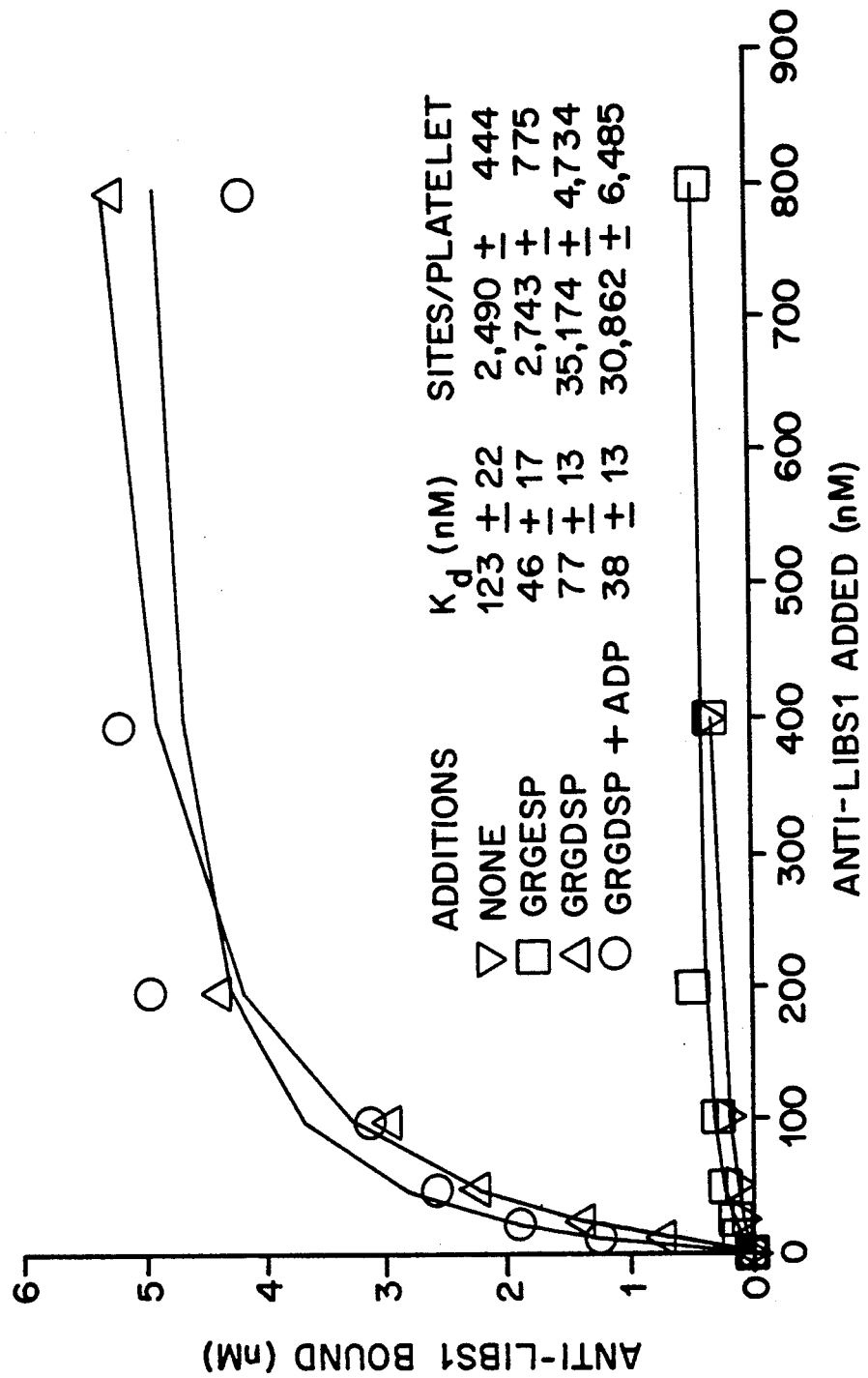
FIG. 2 illustrates anti-LIBS1 binding to platelets expressing a cryptic antigenic determinant as described in Example 5. Varied concentrations of $^{125}$I-anti-LIBS1 were bound at 37° C. for 30 min to gel-filtered platelets in the presence of no peptide (inverted triangle), 0.8 mM GRGESP (squares), 0.8 mM GRGDSP (triangles) or GRGDSP and 10 uM ADP (circles). Bound radioactivity was separated from free by spinning the platelets through a layer of sucrose.

The results are shown in FIG. 2, and are expressed as a plot of the amount of anti-LIBS1 added to the immunoreaction admixture versus the amount of platelet bound anti-LIBS1 detectable after immunoreaction. The results indicate that both stimulated and unstimulated platelets will express a LIBS1 cryptic antigenic determinant in the presence of the RGD-containing ligand GRGDSP. Further, the results indicated about $30-35 \times 10^3$ LIBS1 sites per platelet were detected using LIBS1 specific monoclonal antibody molecules.

Further, the results also indicate the structural specificity of the RGD-containing ligand for GPIIb-IIIa. A conservative substitution exchanging a glutamic acid (E) in place of the normally found aspartic acid residue (D) results in a peptide which is considerably less effective as a cryptic antigenic determinant inducing ligand.

B. Assay for Antibodt Binding to Soluble Purified GPIIb-IIIa That Expresses Cryptic Antigenic Determinants.

The ability of various polypeptide ligands to induce the expression of a cryptic antigenic determinant was studied using soluble isolated GPIIb-IIIa.

To that end, the competition ELISA was performed as described in Example 3B with the following exceptions. Microtiter plates were coated using a coating solution containing isolated GPIIb-IIIa, prepared as described in Example 1B, at a concentration of 10 ug per ml. After blocking, all solutions used were Chelex 100-treated before use, as described for Tyrode's buffer in Example 5A.

Before an antibody composition was added to the GPIIb-IIIa coated microtiter well, 30 ul of a solution of dilution buffer containing (1) 2 mM $CaCl_2$; (2) immunoaffinity isolated GPIIb-IIIa or peptide affinity isolated GPIIb-IIIa, prepared as described in Example 1 and at a concentration of about 40 ug/ml; and (3) polypeptide GRGDSP, or GRGESP, at a final concentration of 1 mM, or no polypeptide, was added to each well. Thereafter, 10 ul of a solution of dilution buffer containing either LIBSa or Mab15 antibody molecules diluted to a limiting concentration as described in Example 3B was admixed into each well to form an immunoreaction admixture. Mab15 is a control antibody molecule that immunoreacts with GPIIb-IIIa but is not an anti-LIBS antibody. The immunoreaction admixtures were maintained at 22° C. for 16–20 hours to permit formation of a first solid phase-bound immunoreaction product between the solid phase-bound GPIIb-IIIa and the admixed antibodies. Thereafter, the amount of immunoreaction product formed was measured by forming a developed color reaction product and detecting the amount of colored product formed as before. Results of the measured immunoreaction is expressed as an apparent GPIIb-IIIa concentration (ug per ml) of the soluble GPIIb-IIIa in the immunoreaction admixture and is calculated as follows. The competition ELISA was first conducted using known GPIIb-IIIa concentrations in the absence of polypeptide to prepare a standard curve of immunoreaction results to obtain A490 measurements using a limiting amount of antibody molecule (i.e., a 1.0 O.D. amount). From the standard curve, any particular A490 measurement can be extrapolated to determine the apparent GPIIb-IIIa concentration present in the immunoreaction admixture. From the above A490 measurements, obtained in the presence of the indicated polypeptides, antibodies and GPIIb-IIIa preparations, apparent GPIIb-IIIa concentrations were calculated and are shown in Table 2.

TABLE 2

| LIBS1 Epitope Expression In Purified GPIIb-IIIa Is Increased By Ligand | | |
|---|---|---|
| | Apparent [GPIIb-IIIa] μg/ml | |
| | LIBSa | Mab 15 |
| Immunoaffinity Purified GPIIb-IIIa | | |
| No Peptide | 7.1 ± 0.8 | 52.2 ± 1.4 |
| GRGDSP (1 mM) | 35.7 ± 5.8 | 56.1 ± 0.2 |
| GRGESP (1 mM) | 12.9 ± 1.9 | 47.7 ± 1.4 |
| RGD-Affinity Purified GPIIb-IIIa | | |
| No Peptide | 23.9 ± 0.4 | 90.5 ± 2.7 |
| GRGDSP (1 mM) | 56.7 ± 1.0 | 95.5 ± 10.7 |
| GRGESP (1 mM) | 30.9 ± 3.2 | 101.7 ± 5.7 |

The results in Table 2 show that RGD-containing polypeptide ligands induce the expression of a cryptic antigenic determinant by GPIIb-IIIa in a manner analogous to that observed using intact platelets (see e.g., FIG. 2). The specificity of ligand-induced expression was verified by using a polypeptide having a conservative substitution (GRGESP), and was further verified by observing no significant ligand influence upon Mab15 monoclonal antibody binding. These results indicate that ligand-induced expression of the cryptic antigenic determinant recognized by an anti-LIBS1 monoclonal antibody (LIBSa) is an intrinsic property of GPIIb-IIIa, and not dependent upon GPIIb-IIIa association with platelets.

EXAMPLE 6

Inhibition of Clot Contraction

Clot contraction is normally dependent upon GPIIb-IIIa and fibrinogen. When the interaction of fibrinogen with GPIIb-IIIa is inhibited by antibodies, clot contraction is inhibited. However, if the binding of fibrinogen to GPIIb-IIIa is inhibited by an RGD-containing peptide that binds to GPIIb-IIIa, clot contraction is enhanced. Thus clot contraction occurs when GPIIb-IIIa is occupied by either fibrinogen or an RGD-containing peptide. Since the binding of either fibrinogen or RGD-containing peptides to GPIIb-IIIa induce the expression of the LIBS1 epitope, the effect of anti-LIBS1 antibody upon clot contraction was studied.

Gel filtered platelets were produced by isolating platelets from acid-citrate dextrose anticoagulated human blood by differential centrifugation and gel filtration on Sepharose 2B and then suspended in a modified Tyrode's buffer at pH 7.3 containing 1 mM $MgCl_2$ and 1% BSA as described in Ginsberg et al., *Blood* 55:661-668 (1980). The gel-filtered platelets ($4 \times 10^8$) were maintained in 0.5 ml of modified Tyrode's buffer at pH 7.3 containing 1 mM $MgCl_2$, 0.5 mM $CaCl_2$, 200 uM RGDS, 1% Bovine Serum Albumin (BSA) and 10 uM adenosine-5,1-diphosphate (ADP) for 5 minutes at 37° C. Various amounts of Fab fragments of LIBSa antibodies were then admixed to the above solution and the resulting solution maintained for 5 minutes at 37° C. An equal volume of a solution containing 50% platelet-poor plasma in a buffer containing 25 mM HEPES (N-[2-hydroxy ethyl]piperazine-N'[ethanesulfonic acid-]at pH 7.2 and 0.15M NaCl and alpha-thrombin (0.5 U/ml) was admixed to the above solution and the resulting mixture was transferred to glass cylinders $7 \times 0.5$ cm internal diameter (ID). The cylinders were capped and then maintained for 8 minutes at room temperature. The resulting clot was poured into a petri dish containing ice cold Tyrode's solution at pH 7.4, and one end was tied to a rigid support and the other end tied to a Grass force displacement transducer, and the isometric tension measured at 37° C. as described in Cohen et al., *Nature*, 246:36-37 (1973).

Figure 3:
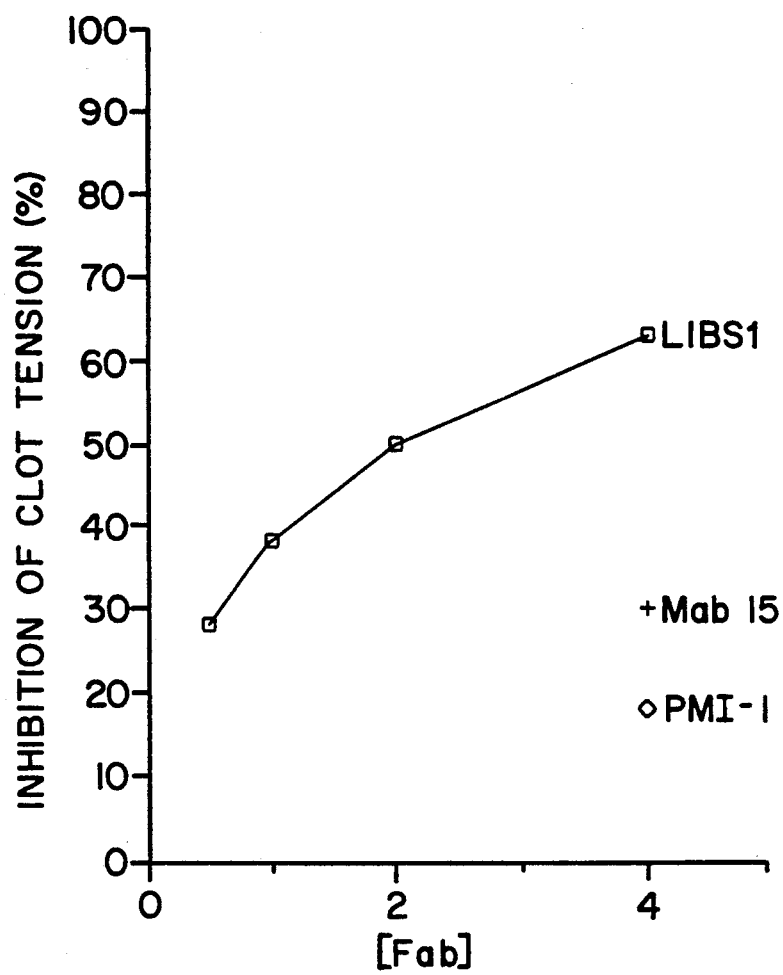
FIG. 3 illustrates anti-LIBS1 inhibition of clot contraction as described in Example 6. Clots were formed from diluted plasma and thrombin in the presence of gel-filtered platelets. The platelets were pre-incubated for 5 min with 200 uM RGDS, and were then incubated another 5 min with the indicated Fabs, LIBSa (LIBS1), anti-GPIIIa antibody (Mab 15) and anti-GPIIb antibody (PMI-1). The clots were then attached to a tensiometer, and the increase in tension over time was observed. Values shown are the percent inhibition of the tension rate (mg/min/cm$^2$ cross sectional area) compared to a clot formed in the absence of Fab.

The results, shown in FIG. 3, indicate that anti-LIBS1 Fab fragments caused a dose-dependent inhibition of the rate of development of isometric clot tension in the presence of an RGDS peptide at a concentration of 200 uM.

EXAMPLE 7

Time-Course For Induction of LIBS1 by GRGDSP

Platelets were maintained in Tyrode's buffer containing 1 mM of the LIBS1-inducing peptide, GRGDSP, or 1 mM of the peptide, GRGESP, for 15 minutes at room temperature before adding an excess of LIBSa (anti-LIBS1). The amount of anti-LIBS1 antibodies bound was determined at various times. Anti-LIBS1 binding in the presence of GRGDSP (circles, FIG. 4) was half-maximal by 0.5 minutes and reached steady state by 5 minutes. A very similar rate of anti-LIBS1 binding was observed (triangles, FIG. 4) when the anti-LIBS1 antibody was added at the same time as the LIBS1-inducing peptide, GRGDSP. These results indicate that the rate limiting step was anti-LIBS1 binding and not the induction of the LIBS1 epitope by the peptide, GRGDSP.

The foregoing specification, including the specific embodiments and Examples, is intended to be illustrative of the present invention and is not to be taken as limiting. Numerous other variations and modifications can be effected without departing from the true spirit and scope of the present invention.

What is claimed is:

1. A diagnostic system in kit form for assaying for the presence of a receptor-ligand complex in a vascular fluid sample, said complex containing a GPIIb-IIIa cell surface receptor and a ligand that are specifically bound, which system comprises:
   a) a package containing, in an amount sufficient to perform at least one assay, a monoclonal antibody composition containing an antibody molecule produced by hybridoma HB10150 that immunoreacts with a ligand-induced binding site on GPIIIa in said receptor-ligand complex but does not immunoreact with the cell surface receptor or the ligand when either is in nonbound form, and
   b) a label for indicating the presence of said antibody molecules in any immunoreaction product.

2. The diagnostic system of claim 1 wherein said label is a radionuclide linked to said antibody molecule.

3. A method of assaying for the presence of a receptor-ligand complex in a vascular fluid sample wherein said complex contains a GPIIb-GPIIIa-containing cell surface receptor specifically bound to a ligand, which method comprises the steps of:
   a) forming an immunoreaction admixture by admixing a vascular fluid sample with a monoclonal antibody composition containing antibody molecules produced by hybridoma HB10150 that immunoreact with a ligand-induced binding site on GPIIIa in said receptor-ligand complex but do not immunoreact with the cell surface receptor or the ligand when either is in non-bound form;
   b) maintaining the admixture for a time period sufficient for said antibodies to immunoreact with any receptor-ligand complex present in the sample and form an immunoreaction product; and
   c) detecting the presence of any immunoreaction product formed in step (b) and thereby the presence of said complex in said sample.

4. The method of claim 3 wherein said cell surface receptor is on a platelet.

5. A method of assaying a platelet-containing vascular fluid sample for the presence of platelets expressing a GPIIb-IIIa-ligand complex, which method comprises the steps of:
   a) forming an immunoreaction admixture by admixing said vascular fluid sample with a monoclonal antibody composition containing antibody molecules produced by hybridoma HB10150 that immunoreact with a ligand-induced binding site expressed on GPIIIa when a complex of GPIIb-IIIa specifically bound to a ligand is formed on said platelets;
   b) maintaining the admixture for a time period sufficient for said antibodies to immunoreact with any ligand-induced binding site expressed on said platelets present in the sample and form an immunoreaction product; and
   c) detecting the presence of any immunoreaction product formed in step (b) as an indication of the presence of platelets expressing a GPIIb-IIIa-ligand complex.

6. The method of claim 5 wherein said GPIIb-IIIa-ligand complex is expressed on fibrinogen-bound platelets.

7. A diagnostic method for detecting clotting disorders comprising:
   a) admixing a platelet-containing fluid sample from a human patient with a sufficient amount of a GPIIb-IIIa-specific ligand to saturate the binding of said ligand to any GPIIb-IIIa-containing cell surface receptor present on said platelets;
   b) adding to said admixture an effective amount of a monoclonal antibody composition with a ligand-induced binding site designated as LIBS1 expressed on GPIIIa on said platelets, said monoclonal antibody composition containing antibody molecules produced by hybridoma HB10150 that immunoreact with a ligand-induced binding site on GPIIIa in said receptor but do not immunoreact with the receptor or the ligand when either is in a non-bound form;
   c) maintaining the admixture for a time period sufficient for said antibodies to react with any ligand-induced binding site expressed on GPIIIa in the sample and form an immunoreaction product;
   d) measuring the amount of any immunoreaction product formed in step (c), and thereby determining the concentration of any ligand-induced binding site expressed on GPIIIa present in said sample; and
   e) comparing the concentration of the expressed ligand-induced binding site determined in step (d) with the concentration of any expressed ligand-induced binding site induced by a saturating amount of said ligand in a normal control fluid sample containing normal platelets obtained from a human who does not have a clotting disorder wherein a lesser concentration of said expressed ligand-induced binding site in said test sample as compared to said normal control sample indicates the presence of a clotting disorder.

8. The method of claim 7 wherein the amount of immunoreaction product formed is measured by use of an indicating means.

9. The method of claim 8 wherein said indicating means is a radionuclide.

10. The method of claim 8 wherein the amount of immunoreaction product formed is measured by use of a specific binding agent in an enzyme-linked immunosorbent assay.

11. The method of claim 7 wherein said GPIIb-IIIa-specific ligand is selected from the group consisting of fibrinogen, an RGD-containing polypeptide ligand, and the gamma chain polypeptide of fibrinogen.

12. The method of claim 11 wherein said RGD-containing polypeptide ligand is GRGDSP.

* * * * *